United States Patent
Yamagata et al.

(10) Patent No.: US 10,109,762 B2
(45) Date of Patent: Oct. 23, 2018

(54) LIGHT SOURCE AND OPTICAL COHERENCE TOMOGRAPHY APPARATUS INCLUDING THE LIGHT SOURCE

(71) Applicant: CANON KABUSHIKI KAISHA, Tokyo (JP)

(72) Inventors: Kenji Yamagata, Sagamihara (JP); Toshimitsu Matsuu, Yokohama (JP); Takeshi Yoshioka, Kawasaki (JP); Takeshi Uchida, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 4 days.

(21) Appl. No.: 14/431,715

(22) PCT Filed: Sep. 26, 2013

(86) PCT No.: PCT/JP2013/005693
§ 371 (c)(1),
(2) Date: Mar. 26, 2015

(87) PCT Pub. No.: WO2014/050102
PCT Pub. Date: Apr. 3, 2014

(65) Prior Publication Data
US 2015/0263219 A1    Sep. 17, 2015

(30) Foreign Application Priority Data
Sep. 28, 2012 (JP) ................................. 2012-217190

(51) Int. Cl.
*H01L 33/00* (2010.01)
*G01B 9/02* (2006.01)
(Continued)

(52) U.S. Cl.
CPC ...... *H01L 33/0045* (2013.01); *G01B 9/02044* (2013.01); *G01B 9/02091* (2013.01);
(Continued)

(58) Field of Classification Search
CPC ...... H01L 33/04; H01L 33/06; H01L 33/0045
See application file for complete search history.

(56) References Cited

U.S. PATENT DOCUMENTS

| | | | | |
|---|---|---|---|---|
| 5,126,803 A | * | 6/1992 | Hager | B82Y 20/00 257/14 |
| 5,585,957 A | * | 12/1996 | Nakao | B82Y 20/00 257/13 |

(Continued)

FOREIGN PATENT DOCUMENTS

| | | |
|---|---|---|
| CN | 1099128 A | 2/1995 |
| CN | 101222118 A | 7/2008 |

(Continued)

OTHER PUBLICATIONS

Ko et al., "Ultrahigh Resolution Optical Coherence Tomography Imaging with a Broadband Superluminescent Diode Light Source", May 17, 2004, Optical Society of America, Optics Express, vol. 12, No. 10, 2112-2119.*

(Continued)

*Primary Examiner* — Joshua King
(74) *Attorney, Agent, or Firm* — Canon USA, Inc. I.P. Division

(57) ABSTRACT

A light source includes an upper electrode layer, a lower electrode layer, and an active layer interposed therebetween. At least one of the upper and lower electrode layers is divided into a plurality of electrodes separated from each other in an in-plane direction of the active layer. The separated electrodes independently inject current into a plurality of different regions in the active layer. The light source emits light by injecting current from the upper and lower electrode layers into the active layer, guide the light in the in-plane direction, and output the light. The plurality of different regions in the active layer include a first region not including a light exit end and a second region including the (Continued)

light exit end, and the second region is configured to emit light of at least first-order level. The active layer has an asymmetric multiple quantum well structure.

16 Claims, 20 Drawing Sheets

(51) Int. Cl.
    *H01L 33/06*     (2010.01)
    *H05B 33/08*     (2006.01)
    *G01N 21/47*     (2006.01)
    *H01L 27/15*     (2006.01)

(52) U.S. Cl.
    CPC .............. *H01L 27/15* (2013.01); *H01L 33/06* (2013.01); *H05B 33/0842* (2013.01); *G01N 21/4795* (2013.01); *H01L 27/153* (2013.01)

(56) References Cited

U.S. PATENT DOCUMENTS

| | | | |
|---|---|---|---|
| 6,628,686 B1* | 9/2003 | Sargent | B82Y 20/00 372/46.01 |
| 2003/0205706 A1 | 11/2003 | Lin et al. | |
| 2004/0196543 A1* | 10/2004 | Akiyama | B82Y 20/00 359/344 |
| 2005/0018201 A1* | 1/2005 | de Boer | A61B 5/0059 356/479 |
| 2005/0105097 A1* | 5/2005 | Fang-Yen | A61B 5/1455 356/497 |
| 2005/0161685 A1* | 7/2005 | Velez | H01L 33/0045 257/85 |
| 2007/0041411 A1* | 2/2007 | Pallec | H01S 5/0265 372/26 |
| 2007/0152225 A1* | 7/2007 | Ooi | B82Y 20/00 257/76 |
| 2010/0259758 A1 | 10/2010 | Asano | |

FOREIGN PATENT DOCUMENTS

| | | |
|---|---|---|
| CN | 101222121 A | 7/2008 |
| CN | 101237122 A | 8/2008 |
| CN | 101566777 A | 10/2009 |
| EP | 0742623 A2 | 11/1996 |
| JP | 10-84130 A | 3/1998 |
| JP | 2000-269600 A | 9/2000 |
| JP | 2007-064912 A | 3/2007 |
| JP | 2007-184557 A | 7/2007 |
| JP | 2008-192731 A | 8/2008 |
| JP | 2009-283736 A | 12/2009 |
| JP | 2012-028570 A | 2/2012 |

OTHER PUBLICATIONS

Li et al., "A High-Performance Quantum Dot Superluminescent Diode with a Two-Section Structure", Dec. 12, 2011, Springer, Nanoscale Research Letters, 6, 625, 1-8.*
A.T. Semenov, et al.; "Spectral Control in Multisection AlGaAs SQW Superluminescent Diodes at 800nm"; Electronics Letters; Feb. 1, 1996; vol. 32, No. 3, pp. 255-256.
X. Li, et al.; "Experimental Investigation of Wavelength-Selective Optical Feedback for a High-Power Quantum Dot Superluminescent Device With Two-Section Structure"; Optics Express; May 2012; vol. 20, No. 11, pp. 11936-11943.
Y.-C. Xin, et al.; "1.3-μm Quantum-Dot Multisection Superluminescent Diodes With Extremely Broad Bandwidth"; IEEE Photonics Technology Letters; vol. 19, No. 7; Apr. 1, 2007; pp. 501-503.
N. Ozaki, et al.; "Multi-Color Quantum Dot Ensembles Grown in Selective-Areas for Shape-Controlled Broadband Light Source"; Journal of Crystal Growth; Dec. 10, 2011; vol. 323, pp. 191-193.
International Search Report and Written Opinion for PCT/JP2013/005693, dated Nov. 26, 2013.
Wang, et al., "Design Considerations for Asymmetric Multiple Quantum Well Broad Spectral Width Superluminescent Diodes", IEEE Journal of Quantum Electronics, Dec. 1, 2008, vol. 44, No. 12, pp. 1256-1262.
The extended European search report for European Application No. 13840219.3-1551/2901500, received on Apr. 14, 2016.

* cited by examiner

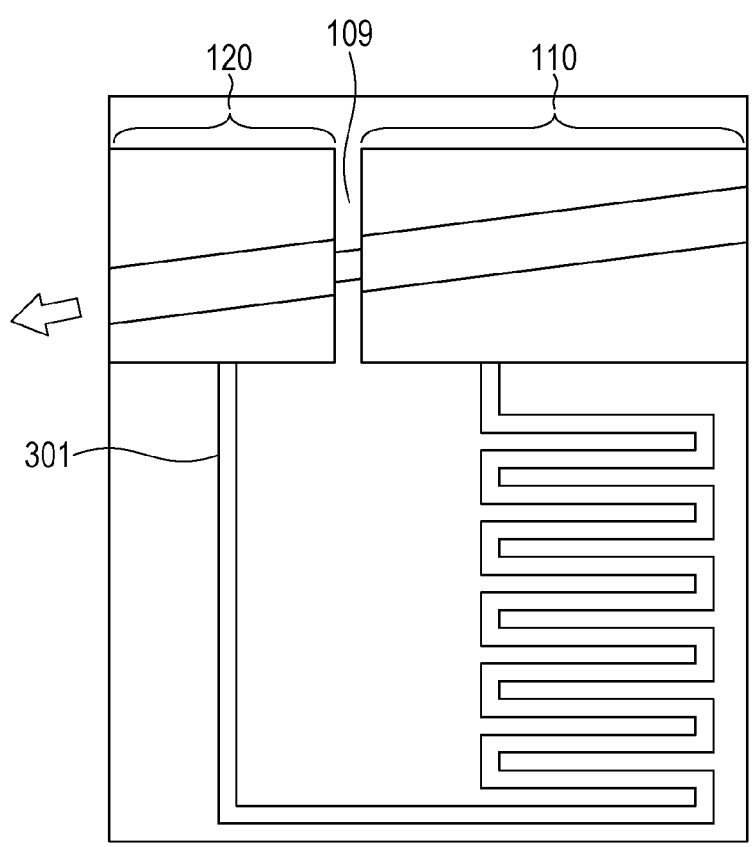

FIG. 13

| ACTIVE LAYER TYPE | LARGEST FULL WIDTH AT HALF MAXIMUM (nm) | CURRENT INJECTION DENSITY (A/cm²) SECOND EMITTING REGION | CURRENT INJECTION DENSITY (A/cm²) FIRST EMITTING REGION | CURRENT DENSITY IN FIRST EMITTING REGION/ CURRENT DENSITY IN SECOND EMITTING REGION (%) | LIGHT OUTPUT WITH NO CURRENT INJECTED INTO FIRST EMITTING REGION (mW) | LIGHT OUTPUT WITH LARGEST FULL WIDTH AT HALF MAXIMUM (mW) |
|---|---|---|---|---|---|---|
| SINGLE QUANTUM WELL STRUCTURE | 68 | 19095 | 1100 | 5.8 | 8.9 | 13 |
| | 68 | 12867 | 653 | 5.1 | 8.3 | 10.5 |
| | 64 | 12815 | 794 | 6.2 | 7.6 | 10.1 |
| | 44 | 5592 | 330 | 5.9 | 4.4 | 4.9 |
| | 60 | 20013 | 1373 | 6.9 | 2.5 | 3.6 |
| | 61 | 24613 | 1190 | 4.8 | 1.7 | 2.2 |
| | 63 | 18218 | 1622 | 8.9 | 1.2 | 1.9 |
| | | 18224 | 1869 | 10.3 | | 2.1 |
| ASYMMETRIC MULTIPLE (DOUBLE) QUANTUM WELL STRUCTURE | 63 | 13859 | 1202 | 8.7 | 1.2 | 1.9 |
| | | 13860 | 1302 | 9.4 | | 2 |
| | 77 | 23504 | 1829 | 7.8 | 0.46 | 0.72 |
| | 61 | 16142 | 904 | 5.6 | 6.6 | 8.9 |
| | 66 | 24036 | 953 | 4.0 | 2.9 | 4.1 |
| | 52 | 20697 | 971 | 4.7 | NO DATA | NO DATA |
| | 65 | 16473 | 672 | 4.1 | 6.1 | 9.1 |
| | 55 | 20743 | 820 | 4.0 | NO DATA | NO DATA |
| | 63 | 13701 | 497 | 3.6 | 9.9 | 11.5 |
| ASYMMETRIC MULTIPLE (TRIPLE) QUANTUM WELL STRUCTURE | 63 | 13695 | 537 | 3.9 | 7.9 | 8.8 |
| | | 13687 | 578 | 4.2 | | 9 |
| | 54 | 9938 | 632 | 6.4 | 11.4 | 15.4 |
| | 55 | 25521 | 1197 | 4.7 | 2.6 | 3.7 |
| | 60 | 19074 | 895 | 4.7 | 3.4 | 5.3 |
| ASYMMETRIC MULTIPLE (QUADRUPLE) QUANTUM WELL STRUCTURE | 53 | 15295 | 566 | 3.7 | NO DATA | NO DATA |
| | | 15297 | 718 | 4.7 | NO DATA | NO DATA |
| | 56 | 24960 | 873 | 3.5 | 4.9 | 6.2 |

FIG. 19

| ACTIVE LAYER STRUCTURE | ASYMMETRIC MULTIPLE QUANTUM WELL STRUCTURE 1 | ASYMMETRIC MULTIPLE QUANTUM WELL STRUCTURE 2 | SINGLE QUANTUM WELL STRUCTURE |
|---|---|---|---|
| LENGTH OF SECOND ELECTRODE (mm) | 0.4 | 0.4 | 0.4 |
| RIDGE WIDTH (micrometers) | 3 | 3 | 3 |
| MINIMUM CURRENT DENSITY NECESSARY FOR FIRST-ORDER LEVEL EMISSION (kA/cm$^2$) | 5.6 | 6.7 | 10.2 |

LIGHT SOURCE AND OPTICAL COHERENCE TOMOGRAPHY APPARATUS INCLUDING THE LIGHT SOURCE

TECHNICAL FIELD

The present invention relates to a light source and an optical coherence tomography apparatus including the light source.

BACKGROUND ART

A super luminescent diode (hereinafter may be abbreviated as SLD) is a semiconductor light source which is capable of providing a relatively high light output of 1 mW or more, like a semiconductor laser, while having a wide spectrum distribution, like a light-emitting diode. Because of its characteristics, the SLD attracts attention in the fields of medicine and measurement where high resolution is required. For example, the SLD is used as a light source for an optical coherence tomography (OCT) apparatus capable of obtaining tomographic images of living tissue.

NPL 1 discloses an SLD having a multi-electrode structure that includes a plurality of electrode pairs in a single SLD device. In the SLD disclosed in NPL 1, a region including an exit end emits light of first-order level and ground level, so that a large peak appears on the lower-wavelength side and a small peak appears on the longer-wavelength side. In this SLD, on the other hand, a region adjacent to the region including the exit end emits light of ground level. This light is combined with that from the region including the exit end described above, so that light output from the SLD has a wide emission wavelength range.

CITATION LIST

Non Patent Literature

NPL 1: ELECTRONICS LETTERS 1st Feb. 1996, Vol. 32, No. 3, pp. 255-256

SUMMARY OF INVENTION

Technical Problem

An active layer of the SLD disclosed in NPL 1 has a single quantum well layer. This means that a minimum current density necessary to emit light of higher energy level is large.

In view of the problem described above, the present invention provides a light source in which a minimum current density necessary to emit light of first-order (higher energy) level is small.

Solution to Problem

A light source according to an aspect of the present invention includes an upper electrode layer, a lower electrode layer, and an active layer interposed therebetween. At least one of the upper electrode layer and the lower electrode layer is divided into a plurality of electrodes separated from each other in an in-plane direction of the active layer. The plurality of separated electrodes are configured to independently inject current into a plurality of different regions in the active layer. The light source is configured to emit light by injecting current from the upper electrode layer and the lower electrode layer into the active layer, guide the light in the in-plane direction, and output the light. The plurality of different regions in the active layer include a first region not including a light exit end and a second region including the light exit end, and the second region is configured to emit light of at least first-order level. The active layer has an asymmetric multiple quantum well structure.

A light source according to another aspect of the present invention includes a semiconductor light-emitting device having two emitting regions, a first emitting region and a second emitting region; and a control unit configured to control current injected into the two emitting regions. The control unit controls the current injected into the first emitting region and the second emitting region such that a density of current injected into the first emitting region is less than 44% of a density of current injected into the second emitting region. Light emitted from the first emitting region and passed through the second emitting region is output from the light source.

An optical coherence tomography apparatus according to another aspect of the present invention includes the light source according to either of the aspects described above; an interference optical system configured to divide light from the light source into reference light and irradiation light for irradiating an object, and generate interference light based on the reference light and reflected light from the irradiated object; a wavelength dispersing unit configured to disperse a wavelength of the interference light; a light detecting unit configured to receive the interference light whose wavelength has been dispersed; and an information obtaining unit configured to obtain information about the object on the basis of an intensity of the interference light.

A method for controlling a light source according to another aspect of the present invention is a method for controlling a light source including a semiconductor light-emitting device having two emitting regions, a first emitting region and a second emitting region. The method includes controlling current injected into the first emitting region and the second emitting region such that a density of current injected into the first emitting region is less than 44% of a density of current injected into the second emitting region, and outputting light emitted from the first emitting region and passed through the second emitting region.

Further features of the present invention will become apparent from the following description of exemplary embodiments with reference to the attached drawings.

BRIEF DESCRIPTION OF DRAWINGS

FIG. 4 is a plan view illustrating a structure of the light source according to a third embodiment of the present invention.

FIG. 13 shows light source configurations, driving conditions, largest full widths at half maximum of emission spectra, and light outputs obtained in EXAMPLE 2.

FIG. 19 is a table showing results of EXAMPLES 8 and 9.

DESCRIPTION OF EMBODIMENTS

Figure 1:
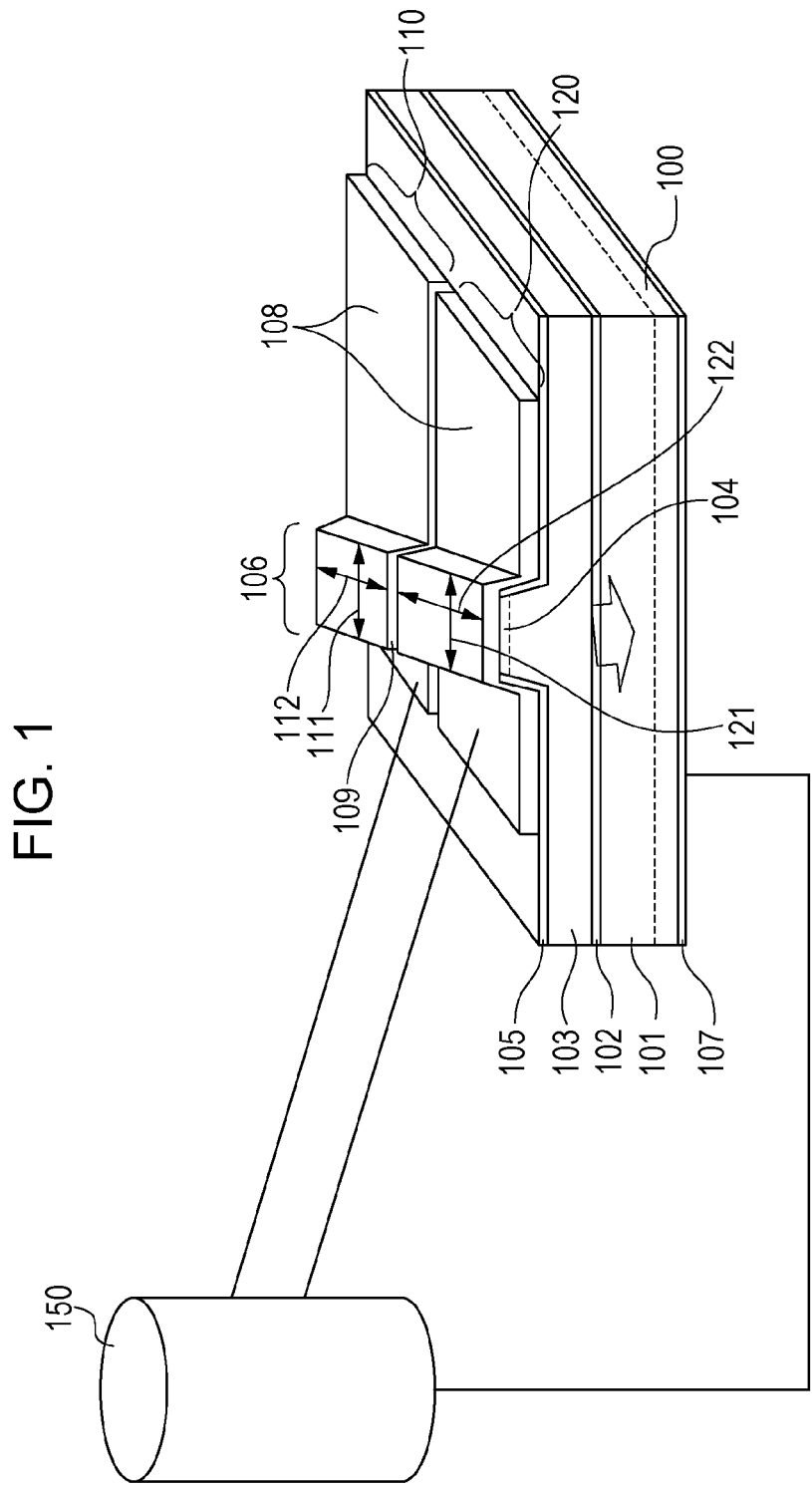
FIG. 1 is a perspective view illustrating a configuration of a light source according to a first embodiment of the present invention.

A light source according to embodiments of the present invention will be described.

A light source according to an embodiment of the present invention includes an upper electrode layer, a lower electrode layer, and an active layer interposed therebetween. The light source has a multi-electrode configuration in which at least one of the upper electrode layer and the lower electrode layer is divided into a plurality of electrodes separated from each other in an in-plane direction of the active layer, specifically in the waveguide direction of light. The plurality of separated electrodes are configured to independently inject current into a plurality of different regions in the active layer. The light source can emit light by injecting current from the upper electrode layer and the lower electrode layer into the active layer, guide the light in the in-plane direction, and output the light. The emission wavelength range is changed by varying the amount of current injected into the active layer. The emission wavelength range can be widened by appropriately adjusting the amount of current injected into the plurality of different regions in the active layer.

The plurality of different regions in the active layer include a first region not including a light exit end and a second region including the light exit end, and the second region is configured to emit light of first-order level and ground level. A peak of first-order level emission appears on the lower-wavelength side, whereas a peak of ground level emission appears on the longer-wavelength side. The emission peak on the longer-wavelength side is smaller than that on the lower-wavelength side. Since the first region is configured to emit light of ground level, the emission wavelength range can be made higher by causing light from the first region to pass through the second region and exit. The present inventors have found that stimulated emission occurs when light from the first region passes through the second region. This means that it is possible to obtain light that has an intensity greater than the sum of the intensity of light emitted from the first region on the longer-wavelength side and the intensity of light emitted from the second region on the longer-wavelength side.

The first region and the second region may be adjacent to each other.

In the light source according to the embodiment of the present invention, the active layer has an asymmetric multiple quantum well structure. To widen the emission wavelength range, light of not only ground level but also first-order level may be emitted. For emission of first-order level, the active layer is configured to have an asymmetric multiple quantum well structure. When the active layer has an asymmetric multiple quantum well structure, it is possible not only to emit light of different emission levels, but also reduce the minimum current density necessary to emit light of first-order level.

In the case of a single quantum well structure, it is necessary to deepen the quantum well to widen the emission wavelength range. However, deepening the quantum well may increase the minimum current density necessary to emit light of first-order level.

In the light source according to the embodiment of the present invention, since the active layer has an asymmetric multiple quantum well structure, it is possible to reduce the minimum current density necessary to emit light of first-order level.

The level of emission may be the first-order level or higher.

The light source according to the embodiment of the present invention may be configured such that a density of current injected into the first region is smaller than a density of current injected into the second region.

For SLD operation in the light source according to the embodiment of the present invention, a carrier density in the second region may be greater than a transparent carrier density.

The second region may have a dominant peak at an energy level higher than that of a dominant peak of light incident on the second region.

A carrier density in a region other than the second region may be greater than a transparent carrier density.

A current density in the second region may be greater than or equal to 80% of a saturated current density.

A light source according to embodiments of the present invention will now be described in detail. An SLD, which is an exemplary semiconductor light-emitting device, will be described as the light source.

First Embodiment

A configuration of a light source according to a first embodiment will now be described with reference to FIG. 1.

The light source according to the present embodiment includes a lower cladding layer 101, an active layer 102, and an upper cladding layer 103 sequentially disposed on a substrate 100. The upper cladding layer 103 is provided with a ridge waveguide 106. An upper electrode 108 is disposed on the ridge waveguide portion, with a contact layer 104 interposed therebetween. Current is injected from the upper electrode 108 and the contact layer 104 into the active layer 102. The upper electrode 108 is divided into two parts, a first electrode 110 and a second electrode 120, spaced apart by a dividing portion 109. Hereinafter, the first electrode 110 and a lower electrode 107 will be referred to as a first electrode pair, and the second electrode 120 and the lower electrode 107 will be referred to as a second electrode pair. Of two (upper and lower) surfaces of the substrate 100, the surface (lower surface) not having the lower cladding layer 101 thereon is provided with the lower electrode 107. The light source according to the present embodiment is an SLD that outputs light in the direction of white arrow in FIG. 1 by applying a voltage between the first and second electrodes 110 and 120 and the lower electrode 107. Hereinafter, such an SLD having a plurality of electrode pairs may be referred to as a multi-electrode SLD.

Figure 2A:
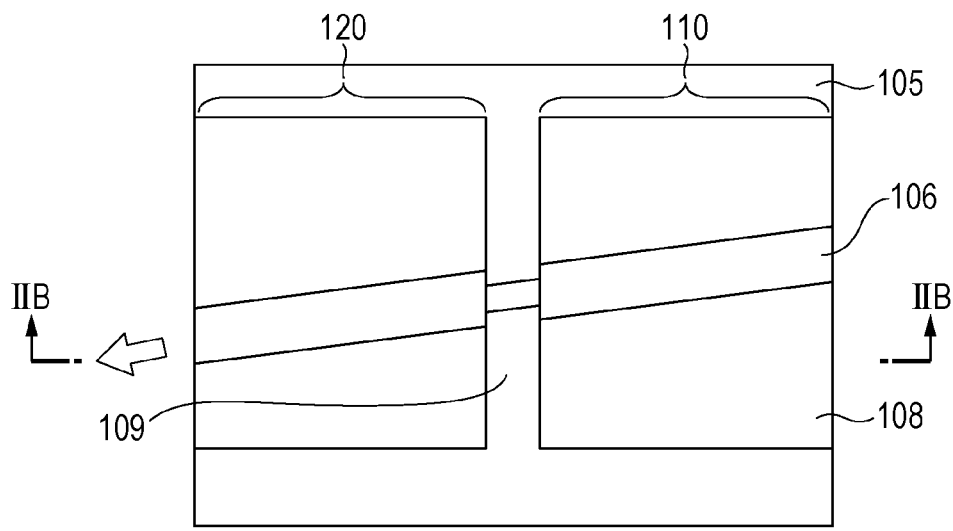
FIG. 2A is a plan view of the light source illustrated in FIG. 1.
Figure 2B:
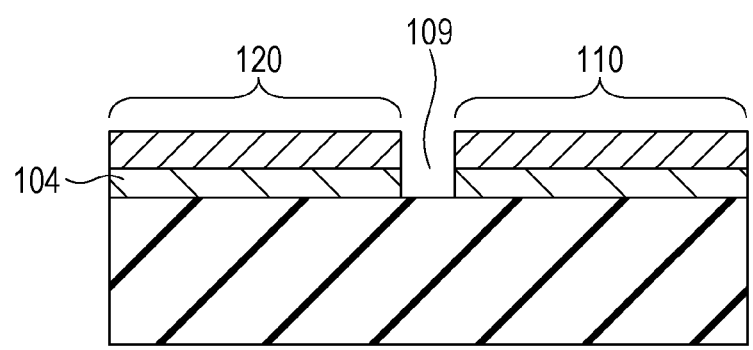
FIG. 2B is a cross-sectional view taken along line IIB-IIB of FIG. 2A.

FIG. 2A is a top view of the light source illustrated in FIG. 1. That is, FIG. 2A illustrates the light source as viewed from the upper electrode 108 formed above the substrate 100. FIG. 2B is a cross-sectional view taken along line IIB-IIB of FIG. 2A. In the example illustrated in FIG. 2B, the contact layer 104 is divided into two parts, which are spaced apart by the dividing portion 109 and electrically separated from each other.

A region of the active layer into which a current is injected by the first electrode 110 is a first emitting region (not shown), and a region of the active layer into which a current is injected by the second electrode 120 is a second emitting region (not shown). The light source of the present embodiment is a super luminescent diode (SLD) having at least two emitting regions (the first emitting region and the second emitting region in the present embodiment). That is, the light source may have three or more emitting regions. In the light source (SLD) of the present embodiment, the first emitting region and the second emitting region may have the same active layer as illustrated in FIG. 1 and FIGS. 2A and 2B, but they may have different active layers, as long as the effects of the present invention can be achieved. When the light source of the present embodiment has three or more emitting regions, these emitting regions may have either the same active layer or different active layers, as long as the effects of the present invention can be achieved. Having the same active layer may mean that different emitting regions share one active layer as illustrated in FIG. 1 and FIGS. 2A and 2B, or may mean that they have different active layers having the same size and composition.

Light from the light source according to the present embodiment is light produced by combining light emitted from the first emitting region and output through the second emitting region, with light emitted from the second emitting region.

The light source of the present embodiment is characterized in that the active layer has an asymmetric multiple quantum well structure. The light source of the present embodiment is also characterized in that light of higher energy level is emitted from the second emitting region, whereas light of lower energy level is emitted from an emitting region (regions) other than the second emitting region.

When the active layer has an asymmetric multiple quantum well structure, light of higher energy level can be emitted at a lower current density than in the case of an active layer having a single quantum well structure. This is because when the active layer has an asymmetric multiple quantum well structure, it is possible to form a shallow emission level while having a plurality of emission levels. A single quantum well structure requires a high carrier density for emitting light of higher energy level. On the other hand, in an asymmetric multiple quantum well structure, where there is a shallow well of higher energy level even at a ground level, it is possible to emit light of higher energy level even at a low carrier density.

In the present embodiment, since different spectra are produced by varying the current density from one emitting region to another, the structure of the active layer does not have to be changed depending on the emitting region. This simplifies the process of making the device, and improves yield.

Second Embodiment

Figure 3A:
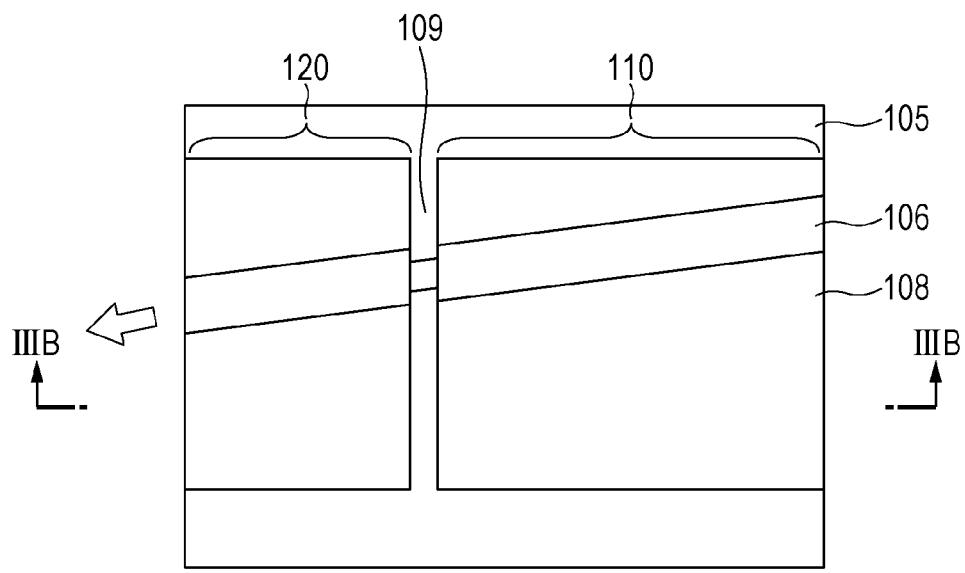
FIG. 3A is a plan view illustrating a structure of a light source according to a second embodiment of the present invention.
Figure 3B:
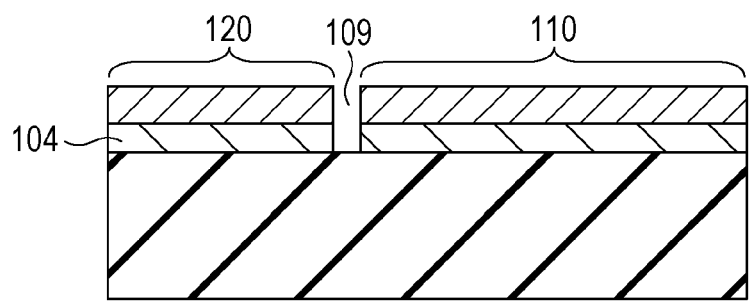
FIG. 3B is a cross-sectional view taken along line IIIB-IIIB of FIG. 3A.

A light source according to a second embodiment of the present invention will now be described with reference to FIGS. 3A and 3B.

In the first embodiment described above, the first electrode 110 and the second electrode 120 have the same length in the waveguide direction. In the present embodiment, the first electrode 110 is longer than the second electrode 120 in the waveguide direction.

For a multi-electrode SLD to realize a higher output and a wider emission wavelength range, light of higher energy level is emitted from the second emitting region and light of lower energy level is emitted from an emitting region (regions) other than the second emitting region. Specifically, light of higher energy level may be emitted from the second emitting region and light of lower energy level may be emitted from the first emitting region. Here, there are no particular restrictions on emitting regions other than the first and second emitting regions.

When the first electrode 110 is longer in the waveguide direction, it is possible not only to lower the current density in the first emitting region, but also to facilitate fine adjustment of the current density. Since light from the first emitting region is amplified by passing through the second emitting region, the emission spectrum changes significantly depending on the density of current injected by the first electrode 110 into the first emitting region. Thus, since it is necessary to finely adjust the current density in the first electrode 110 while observing the spectrum, it is very advantageous that the first electrode 110 be longer in the waveguide direction.

Third Embodiment

A light source according to a third embodiment of the present invention will be described.

The light source of the present embodiment is characterized in that it includes a control unit (indicated by reference numeral 150 in FIG. 1) that controls current injected into two emitting regions, a first emitting region and a second emitting region, such that the density of current injected into the first emitting region is less than 44% of the density of current injected into the second emitting region.

A mechanism will be described, which increases the full width at half maximum of the emission spectrum of the light source according to the present embodiment.

The function of the second emitting region is to emit light of higher energy level.

This means that if the active layer structure is a single quantum well structure or a well structure including multiple wells of the same level, light of higher-order (first-order) level is emitted, whereas if the active layer structure is an asymmetric multiple quantum well structure, light of higher energy level is emitted therefrom. The asymmetric multiple quantum well structure may include a well capable of emitting light of higher-order level. Therefore, the active layer of the second emitting region may include a quantum well capable of emitting light at two or more different quantum levels, or include a quantum well capable of emitting light at a single but higher-order level. Also, a current (relatively large current) which allows emission of higher energy level may be injected into the second emitting region. A spectrum of a higher energy level appears in the shorter-wavelength range.

The function of the first emitting region is to emit light of ground (zero-order) level. If there are wells of multiple levels, the function of the first emitting region is to emit light of lower energy level. The spectrum of the lower energy level appears in the longer-wavelength range. Here, the amount of current injected into the first emitting region needs to be kept low. This is because if the amount of current injected into the first emitting region increases, a wavelength shift occurs in the direction in which the emission component of a higher energy level increases. Generally, a small amount of current injection produces a very small light output. However, in an SLD having a multi-electrode structure, such as the light source of the present embodiment, a small amount of light of lower energy level emitted from the first emitting region is amplified by passing through the second emitting region. This causes a spectrum of large output to appear in the longer-wavelength range. As a result, a spectrum of a higher energy level covers the shorter-wavelength range, and a spectrum of a lower energy level covers the longer-wavelength range. Thus, a wide emission spectrum can be obtained.

A state in which a higher energy level spectrum and a lower energy level spectrum are balanced corresponds to the state in which "the density of current injected into the first emitting region is less than 44% of the density of current injected into the second emitting region" in the present embodiment. When the light source emits light in such a state, the emitted light has an emission spectrum having a substantially Gaussian shape and a wide full width at half maximum.

If a current having a current density greater than or equal to 44% of that in the second emitting region is injected into the first emitting region, a spectrum component of a lower energy level increases rapidly (in response to amplification). Thus, a major component of the emission spectrum is shifted to the longer-wavelength side, and the full width at half maximum is narrowed. Or, the emission spectrum may be divided into a higher energy level peak and a lower energy level peak that form a spectrum having a multimodal shape, not a substantially Gaussian shape. The behaviors described above are substantially the same, regardless of whether the active layer structure is a single quantum well structure or a multiple quantum well structure.

As described above, the function of the first emitting region is to emit light of lower energy level. However, it is known that even if current injected into the first emitting region is a weak current having a current density less than 44% of that of current injected into the second emitting region, a spectrum produced in the first emitting region includes a few components of higher energy level and is shifted toward the shorter-wavelength side. If there are third, fourth, and subsequent emitting regions different from the first and second emitting regions, the third, fourth, and subsequent emitting regions may allow a part of the lower energy level on the longer-wavelength side (i.e., a part of the gain spectrum closest to the longer-wavelength range) to appear and be amplified in the first and second emitting regions, so that the longer-wavelength side can be covered.

The control unit may control current injected into the first emitting region and the second emitting region such that the ratio of the density of current injected into the first emitting region to the density of current injected into the second emitting region is less than or equal to 14%, preferably greater than or equal to 0%, more preferably less than or equal to 11%, and still more preferably greater than or equal to 3%.

The output and shape of the emission spectrum is mainly determined by the ratio between densities of current injected into the first and second emitting regions described above. By injecting current into the third and subsequent emitting regions, it is possible to further increase the full width at half maximum of the spectrum, and to make fine adjustment of the light output and the shape of the spectrum. Note that there are no particular restrictions on the ratio of the density of current injected into the third and subsequent emitting regions.

Substantially Gaussian Shape

The above description states that an emission spectrum has a substantially Gaussian shape. This means that the second largest peak value of a point spread function of the emission spectrum is less than or equal to 30% of the largest peak value. The second largest peak value is preferably less than or equal to 20% of the largest peak value, and more preferably less than or equal to 10% of the largest peak value.

A point spread function of an emission spectrum (with the horizontal axis representing the wavelength and the vertical axis representing the emission intensity) is a function obtained by converting the horizontal axis of the emission spectrum to the wave number and applying the Fourier transform.

A part of the point spread function, the part including a peak other than the largest peak value, is called a side lobe. If the peak of the side lobe is large, it is difficult for the OCT apparatus to obtain an accurate tomographic image.

First Emitting Region, Second Emitting Region

In the present embodiment, the first emitting region is a region of the active layer into which current is injected by the first electrode 110. Also in the present embodiment, the density of current injected into the first emitting region is a value obtained by dividing a value of current injected into the first electrode 110 by an area of the first electrode 110 (or the product of a value of a ridge width 111 and a value of an element length 112).

Similarly, in the present embodiment, the second emitting region is a region of the active layer into which current is injected by the second electrode 120. Also in the present embodiment, the density of current injected into the second emitting region is a value obtained by dividing a value of current injected into the second electrode 120 by an area of the second electrode 120 (or the product of a value of a ridge width 121 and a value of an element length 122).

In the present embodiment, the first emitting region and the second emitting region each independently have any of a single quantum well structure, a multiple quantum well structure, and an asymmetric multiple quantum well structure, and include a quantum well capable of emitting light at two or more different quantum levels.

Active Layer

In the present embodiment, the active layer serving as an emitting region may have a quantum well structure. Specifically, the active layer of the present embodiment may have either a single quantum well structure or a multiple quantum well structure (either a symmetric or asymmetric multiple quantum well structure). The optimum current density ratio that produces the largest full width at half maximum varies depending on the active layer structure and the element length. However, under any of such conditions, an emission spectrum having a substantially Gaussian shape and a wide full width at half maximum can be obtained, as long as the density of current injected into the first emitting region is less than 44% of the density of current injected into the second emitting region. That is, the current density ratio may be determined such that the density of current injected into the first emitting region is less than 44% of the density of current injected into the second emitting region, by taking the full width at half maximum, the shape of the emission spectrum, and the intensity of light output into consideration.

The quantum well structure suitable for the active layer varies depending on the wavelength of light to be emitted. The emission wavelength of the quantum well structure is determined by materials of a well layer and a barrier layer, and the thickness of the well layer. In the following example, as a quantum well that emits light having a suitable wavelength, a wavelength of ground level emission of a quantum well structure will be mainly described.

For example, for ground level emission to be located in the wavelength range of 800 nm to 850 nm, $Al_xGa_{(1-x)}As$ with an Al composition x ranging from 0 to 0.15 may be used to form a well layer. AlGaAs with an Al composition higher than that of the well layer may be used to form a barrier layer. Here, the quantum well layer may be 5 nm to 10 nm thick. The wavelength of ground level emission is determined by the thickness and the material of the well layer. Therefore, the wavelength range described above may also be realized by making the well layer thinner than 5 nm and using a material having a wavelength corresponding to a smaller band bap, accordingly.

For ground level emission to be located in the wavelength range of 850 nm to 900 nm, $In_xGa_{(1-x)}As$ with an In composition ranging from 0 to 0.1 may be used to form a well layer. GaAs or AlGaAs may be used to form a barrier layer. The well layer may be 5 nm to 10 nm thick. The wavelength of ground level emission is determined by the thickness and the material of the well layer. Therefore, the wavelength range described above may also be realized by making the well layer thinner than 5 nm and using a material having a wavelength corresponding to a smaller band bap, accordingly.

The materials used to realize the 800 nm to 900 nm wavelength range are not limited to those described above, and any other materials that emit light in this wavelength range may be used. For example, GaInAsP may be used to form the well layer and realize the quantum well structure based on the concepts described above.

For other wavelength ranges, the active layer may also be realized by using a well layer that emits light in each wavelength range and a barrier layer made of a material with a band gap wider than that of the well layer, and adjusting the width of the well layer. For example, for the 980 nm range, InGaAs with an In composition of about 0.2 may be used to form a well layer. For the 1550 nm range, InGaAs having an In composition of about 0.68 and lattice-matched with an InP substrate may be used to form a well layer.

One or more of the quantum well structures described above may be used as the active layer of the SLD. When multiple quantum well layers are used, light may be emitted in a wider wavelength range by using quantum well structures having a plurality of different emission wavelengths.

The active layer described above has a quantum well structure, which is suitable for use in the SLD because of its gain characteristics and ease of manufacture. However, the active layer structure of the SLD is not limited to a quantum well structure. For example, an active layer having a so-called bulk structure with a thickness which can reduce the quantum effect, or an active layer having a quantum wire or quantum dot structure may be used.

(Examples of Current Density Control)

Examples of current density control will be described, which is performed such that the density of current injected into the first emitting region is less than 44% of the density of current injected into the second emitting region.

(Example 1) FIG. 4 is a plan view of the light source according to the present embodiment, as viewed in the same direction as in FIG. 2A. In this example, the first electrode 110 and the second electrode 120 are electrically connected to each other by a metal wire 301, such as an Au wire, which is a resistance wire. That is, except that the first electrode pair and the second electrode pair are electrically connected to each other by a resistance wire, the configuration illustrated in FIG. 4 is the same as that illustrated in FIGS. 2A and 2B. The metal wire 301 serves as an electrical resistance. That is, the light source illustrated in FIG. 4 is configured such that current is injected, through a metal wire for current injection from a power supply to the second emitting region and a resistance wire extending from the metal wire, into the first emitting region. When the length of the metal wire is appropriately set and current is injected into the second electrode 120, a current smaller than that injected into the second electrode 120 is injected into the first electrode 110. Thus, the density of current injected into the first emitting region can be made less than 44% of the density of current injected into the second emitting region.

Figure 5A:
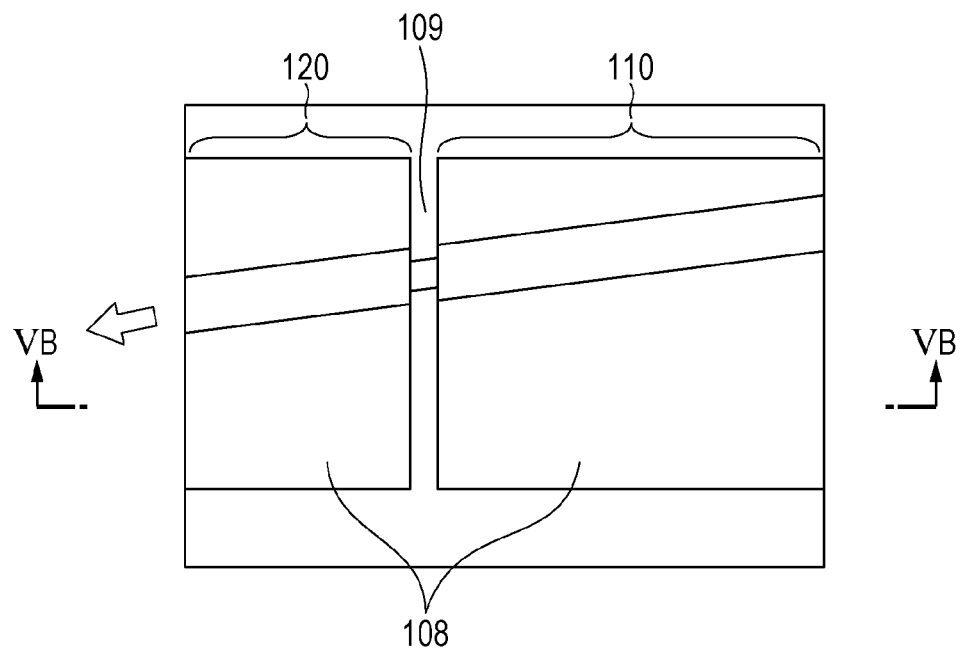
FIG. 5A is a plan view illustrating another structure of the light source according to the third embodiment.
Figure 5B:
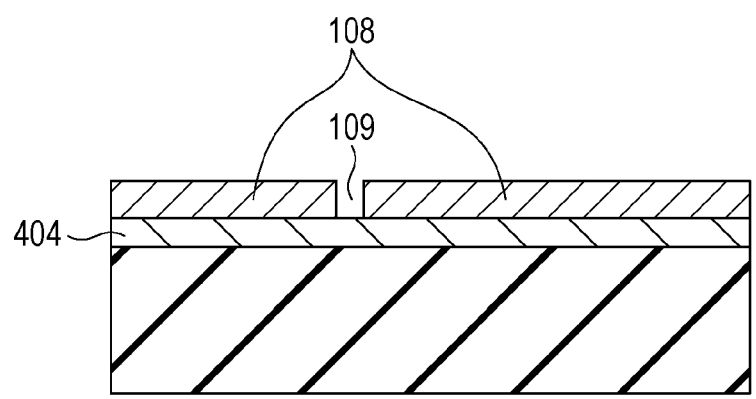
FIG. 5B is a cross-sectional view taken along line VB-VB of FIG. 5A.

(Example 2) FIG. 5A is a plan view of the light source according to the present embodiment, as viewed in the same direction as in FIG. 2A. FIG. 5B is a cross-sectional view taken along line VB-VB of FIG. 5A. In the example illustrated in FIG. 5B, a contact layer 404, which is a semiconductor layer, is not divided into separate parts. That is, except that the first electrode pair and the second electrode pair are electrically connected to each other by a semiconductor layer, the configuration illustrated in FIGS. 5A and 5B is the same as that illustrated in FIGS. 2A and 2B. The resistance of the contact layer 404 serves as an electrical resistance, as in the case of the metal wire in the example of FIG. 4. The light source illustrated in FIGS. 5A and 5B is configured such that current is injected, through a metal wire for current injection from a power supply to the second emitting region and a resistance wire extending from the metal wire, into the first emitting region. Therefore, by appropriately setting the composition and size of the contact layer 404, the density of current injected into the first emitting region can be made less than 44% of the density of current injected into the second emitting region, as in Example 1 of FIG. 4.

Figure 6:
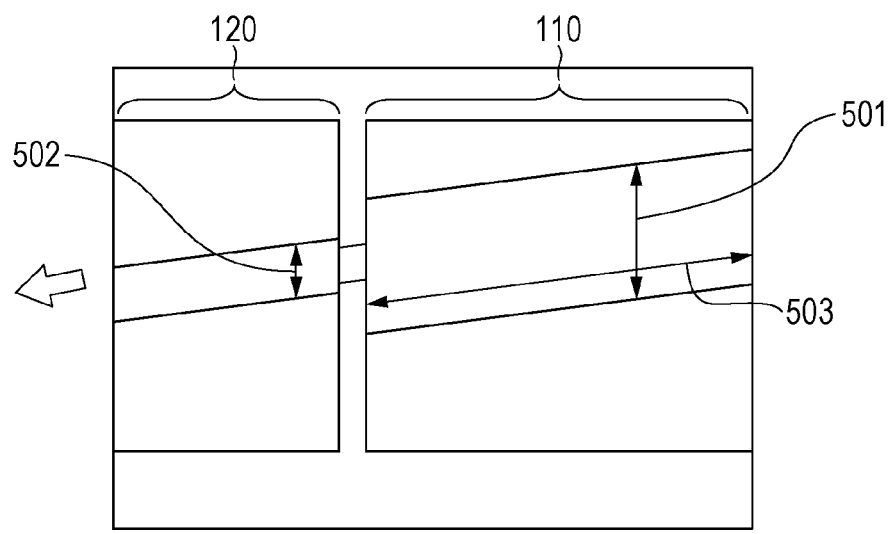
FIG. 6 is a plan view illustrating still another structure of the light source according to the third embodiment.

(Example 3) FIG. 6 is a plan view of the light source according to the present embodiment, as viewed in the same direction as in FIG. 2A. In the example illustrated in FIG. 6, a ridge width 501 of the first electrode 110 is greater than a ridge width 502 of the second electrode 120. By appropriately varying the ridge widths of the first electrode 110 and the second electrode 120, it is possible to change the amount of current injected into the first and second emitting regions, and change the full width at half maximum of the spectrum of light emitted from the light source.

Increasing the area of the first electrode 110 can increase the amount of current injected into the first emitting region. However, increasing an element length 503 may produce an emission spectrum having a multimodal shape, not a substantially Gaussian shape. By increasing the ridge width 501, it is possible to increase the amount of current injected into the first emitting region and maintain the substantially Gaussian shape.

Fourth Embodiment: Four-Electrode SLD

The first to third embodiments have described configurations that use two electrodes for current injection. The fourth embodiment will describe a configuration that uses four electrodes, with reference to FIG. 7. Note that the description of matters common to those in the first to third embodiments will be omitted, and matters different from those in the first to third embodiments will be described.

Figure 7:
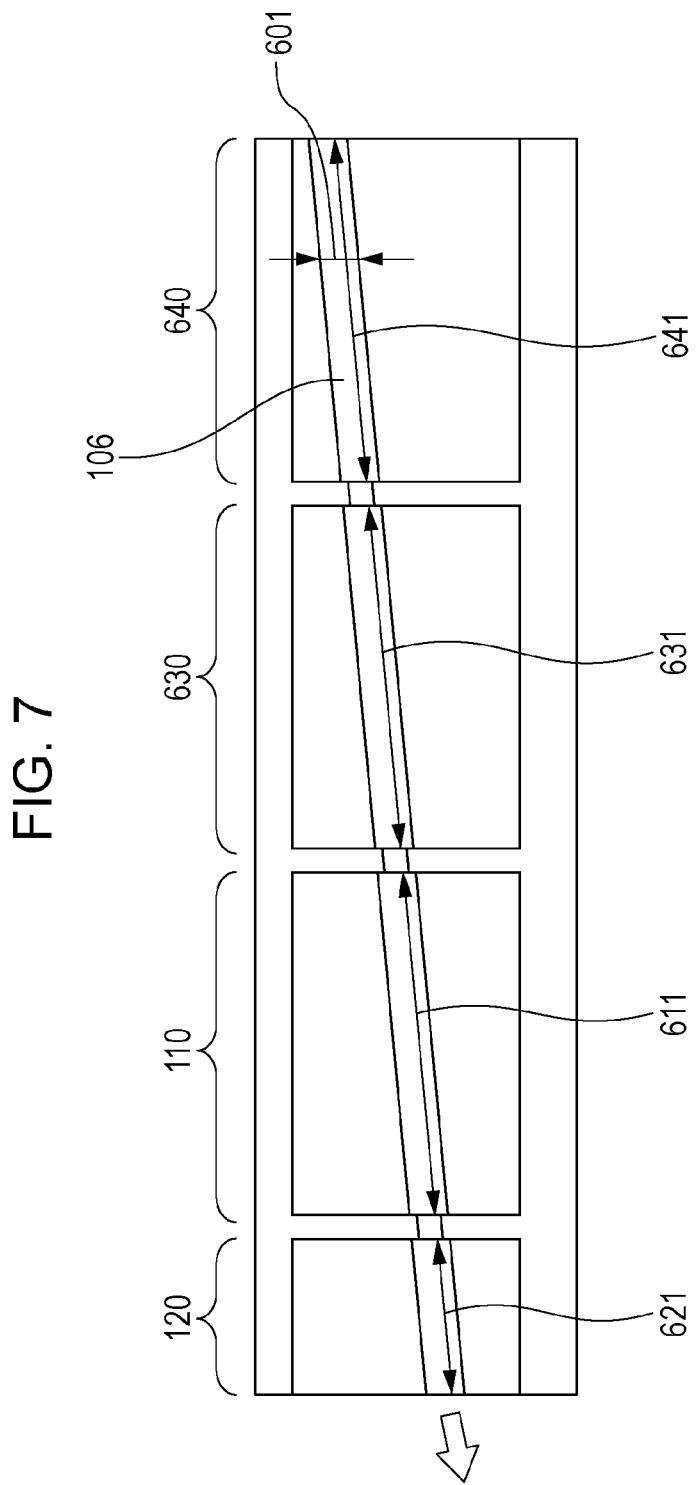
FIG. 7 is a plan view illustrating a structure of a light source according to a fourth embodiment of the present invention.

Like FIG. 2A, FIG. 7 illustrates the light source as viewed from the upper electrode formed above the substrate. In the present embodiment, the light source includes a third electrode 630 and a fourth electrode 640 in addition to the first electrode 110 and the second electrode 120 described above. The output and shape of the emission spectrum is mainly determined by the densities of current injected into the first and second emitting regions. By injecting current into the third and fourth emitting regions corresponding to the third and fourth electrodes 630 and 640, respectively, it is possible to further increase the full width at half maximum of the spectrum, and to make fine adjustment of the light output and the shape of the spectrum.

By making the density of current injected into the first emitting region less than 44% of the density of current injected into the second emitting region, the light source of the present embodiment can also realize an emission spectrum having a substantially Gaussian shape and a wide full width at half maximum.

Also, by providing the third electrode 630 and the fourth electrode 640 and injecting current into them, it is possible to achieve a high light output even when the amount of current injected into the first electrode 110 is small. Therefore, when there are three or more electrodes, the density of current injected into the first emitting region and the second emitting region may be controlled such that the density of current injected into the first emitting region is less than or equal to 2% of the density of current injected into the second emitting region.

The configuration that uses four electrodes has been described. Even with a configuration that uses three, five, or more electrodes, it is possible to realize a light source that emits light having an emission spectrum that has a substantially Gaussian shape and a wide full width at half maximum, by making the density of current injected into the first emitting region less than 44% of the density of current injected into the second emitting region.

Fifth Embodiment: CT Apparatus

Figure 8:
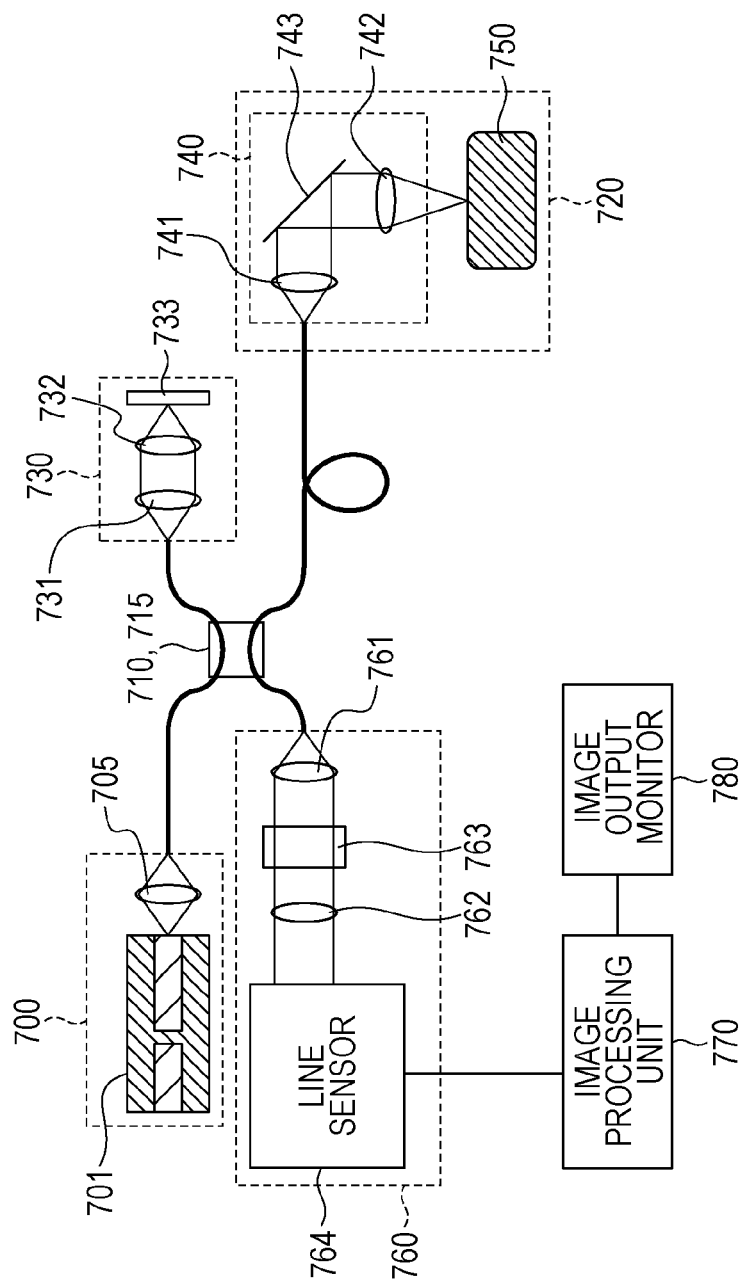
FIG. 8 illustrates an OCT apparatus according to a fifth embodiment of the present invention.

With reference to FIG. 8, a fifth embodiment will describe an optical coherence tomography (OCT) apparatus that includes a light output unit 700, a light dividing unit 710, a reference light reflecting unit 730, a measuring unit 720, a light detecting unit 760, an image processing unit (information obtaining unit) 770, and an image output monitor 780. A light source 701 included in the light output unit 700 is a light source according to any of the embodiments described above.

Light from the light source 701 is divided by the light dividing unit 710 into reference light and irradiation light for irradiating a measuring object 750. The light dividing unit 710 generates interference light based on the reference light and reflected light from the irradiated measuring object 750. Light returned from the reference light reflecting unit 730 and the measuring unit 720 passes through an interference unit 715 and enters the light detecting unit 760. Information obtained by the light detecting unit 760 is converted to an image by the image processing unit 770 for conversion into a tomographic image, and is displayed as a tomographic image by the image output monitor 780 which includes, for example, a display screen of a personal computer.

The OCT apparatus of the present embodiment will now be described in detail by using an example.

The OCT apparatus illustrated in FIG. 8 includes the light output unit 700, the light dividing unit 710 that divides light from the light output unit 700 into reference light and measuring light, the reference light reflecting unit 730, the measuring unit 720 including the measuring object 750 and an irradiation optical system 740 for irradiating the measuring object 750, the interference unit 715 that allows interference of the reflected reference light with the reflected measuring light, the light detecting unit 760 that detects interference light obtained by the interference unit 715, the image processing unit 770 that obtains information of a tomographic image based on the light detected by the light detecting unit 760, and the image output monitor 780 that displays the tomographic image.

Light from the light output unit 700 passes through an optical fiber to reach the light dividing unit 710, which divides the light into reference light and measuring light. The reference light enters the reference light reflecting unit 730. The light dividing unit 710 and the interference unit 715 use the same fiber coupler.

The reference light reflecting unit 730 includes collimator lenses 731 and 732 and a reflecting mirror 733. In the reference light reflecting unit 730, the reference light passes through the collimator lenses 731 and 732 to reach the reflecting mirror 733, reflects off the reflecting mirror 733, and returns to the optical fiber. The measuring light, which is the other of the two beams of light obtained by the light dividing unit 710, passes through an optical fiber and enters the measuring unit 720. The irradiation optical system 740 in the measuring unit 720 includes collimator lenses 741 and 742 and a reflecting mirror 743 for bending an optical path by 90 degrees. The irradiation optical system 740 directs light that has entered the irradiation optical system 740 to the measuring object 750 and causes the reflected light to be coupled to the optical fiber again.

The light returned from the reference light reflecting unit 730 and the measuring unit 720 passes through the interference unit 715 and enters the light detecting unit 760. The light detecting unit 760 includes collimator lenses 761 and 762, a spectroscope (wavelength dispersing unit) 763, and a line sensor 764 for obtaining spectrum information of light dispersed by the spectroscope 763. The wavelength dispersing unit 763 uses a grating. The light detecting unit 760 is configured to obtain spectrum information of light that has entered the light detecting unit 760. The light output unit 700 may include a lens 705.

The information obtained by the light detecting unit 760 is transmitted to the image processing unit 770 that obtains tomographic image information. Thus, tomographic image information, which is a final output, can be obtained. The information is displayed as a tomographic image on the image output monitor 780 which includes, for example, a display screen of a personal computer.

The OCT apparatus of the present embodiment is characterized by the light source 701. For example, when the light source (two-electrode SLD) described in the first embodiment is used and a current of 110 mA (18.3 kA/cm$^2$) and a current of 14 mA (1.75 kA/cm$^2$) are injected into the first emitting region and the second emitting region, respectively, it is possible to output a wide spectrum and thus to obtain tomographic image information having a high resolution. This OCT apparatus is useful for tomographic imaging, for example, in ophthalmology, dentistry, and dermatology.

Sixth Embodiment: Method for Controlling Light Source

A sixth embodiment will describe a method for controlling a light source.

The method for controlling a light source according to the present embodiment is a method for controlling a light source that includes a super luminescent diode having two emitting regions. This method is characterized in that it includes the steps of controlling current injected into the first emitting region and the second emitting region such that the density of current injected into the first emitting region is less than 44% of the density of current injected into the second emitting region, and outputting light emitted from the first emitting region and passed through the second emitting region.

EXAMPLES

EXAMPLES of the present invention will be described. Active layer structures (types), ridge widths, and element lengths described below are merely examples and are not intended to be limiting. An SLD, which is a semiconductor light-emitting device, will be described as a light source.

Example 1

Asymmetric Multiple Quantum Well Structure: Example of Two-Electrode SLD

A configuration of an SLD to which the present invention is applied will be described with reference to the perspective view of FIG. 1 and the plan view of FIG. 2A. In EXAMPLE 1, in the first embodiment (FIG. 1 and FIGS. 2A and 2B), an n-type GaAs substrate was used as the substrate 100, an n-type cladding layer (n-Al$_{0.5}$GaAs, 1.2 micrometers thick) was used as the lower cladding layer 101, a p-type cladding layer (n-Al$_{0.5}$GaAs, 1 micrometer thick) was used as the upper cladding layer 103, and a p-type contact layer (p-GaAs doped with carbon (C) impurities at a concentration of $5 \times 10^{19}$ cm$^{-3}$, 0.2 micrometers thick) was used as the contact layer 104. The active layer 102 having an asymmetric multiple quantum well structure (asymmetric double quantum well structure) composed of two depth-modulated quantum wells was used. Specifically, the active layer 102 includes two 8-nm-thick InGa$_{(1-x)}$As (x=0.03, 0.05) well layers and two barrier layers (Al$_{0.1}$GaAs, 8 nm thick) alternately disposed.

The ridge portion (ridge waveguide) 106 was formed into a structure having a ridge width of 4 micrometers and a height of 0.8 micrometers, by forming a striped resist pattern using a photolithographic technique and then partially etching the contact layer 104 and the upper cladding layer 103.

After a 0.4-micrometer-thick SiO$_2$ film 105, which is an insulating film, was formed by sputtering over the entire surface of the upper cladding layer 103 and the contact layer 104, only a portion of the contact layer 104 in the upper part of the ridge was exposed, and the upper electrode 108 was formed by a liftoff process. Next, the lower electrode 107 was formed on the entire lower surface of the substrate 100. The upper electrode 108 and the lower electrode 107, which are a Ti (50 nm)/Au (300 nm) stacked film and an AuGe (150 nm)/Ni (30 nm)/Au (200 nm) stacked film, respectively, were formed by a vacuum evaporation method.

Last, to allow the first electrode 110 and the second electrode 120 to be independently driven, the upper electrode 108 and the contact layer 104 were partially removed by etching at the dividing portion 109 in the photolithography and etching process. Thus, the upper electrode 108 was divided into the first electrode 110 and the second electrode 120.

The element lengths of the first electrode 110 and the second electrode 120 electrically separated from each other were 0.2 mm and 0.15 mm, respectively. The separation width between the electrodes was 10 micrometers.

To prevent reflection of emitted light, the ridge portion 106 was structured such that the longitudinal direction thereof was inclined 7 degrees from the normal to an end face (cleavage plane) thereof.

Figure 9A:
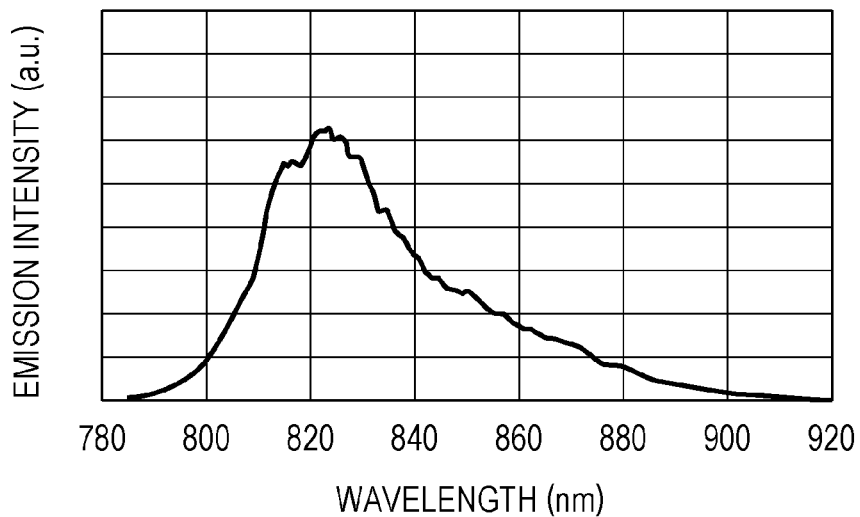
FIG. 9A is a graph of an emission spectrum obtained in EXAMPLE 1 of the present invention.
Figure 9B:
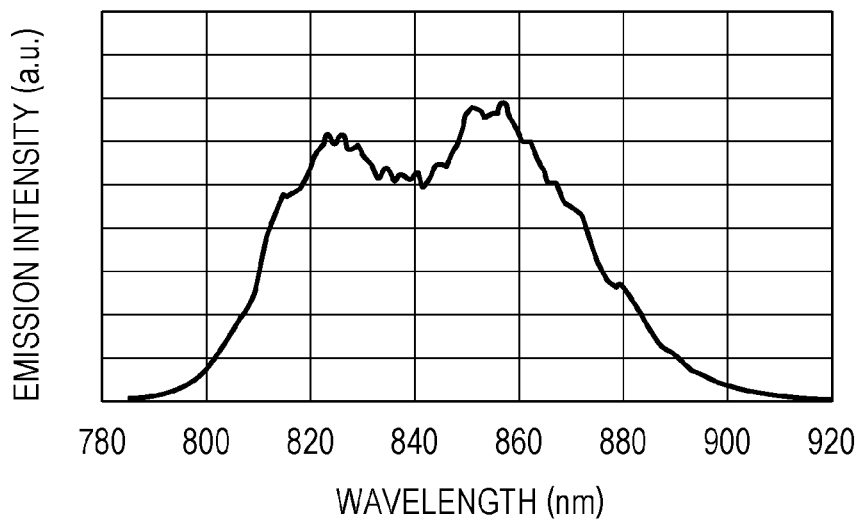
FIG. 9B is a graph of another emission spectrum obtained in EXAMPLE 1.

Light-emitting characteristics of the light source formed by the process described above are shown in FIGS. 9A and 9B. FIG. 9A shows an emission spectrum obtained when a current of 110 mA (current density: 18.3 kA/cm$^2$) was injected into only the second emitting region. The full width at half maximum of this emission spectrum was 30 nm and the output was 1.2 mW. FIG. 9B shows an emission spectrum obtained when a current of 110 mA (18.3 kA/cm$^2$) was injected into the second emitting region and a current of 14 mA (1.75 kA/cm$^2$) was injected into the first emitting region. The full width at half maximum of this emission spectrum was 64 nm and the output was 2.1 mW. That is, by injecting a current into the first emitting region at a current density about 9.6% of that for the second emitting region, both the full width at half maximum of the spectrum and the light output were roughly doubled.

Figure 10:
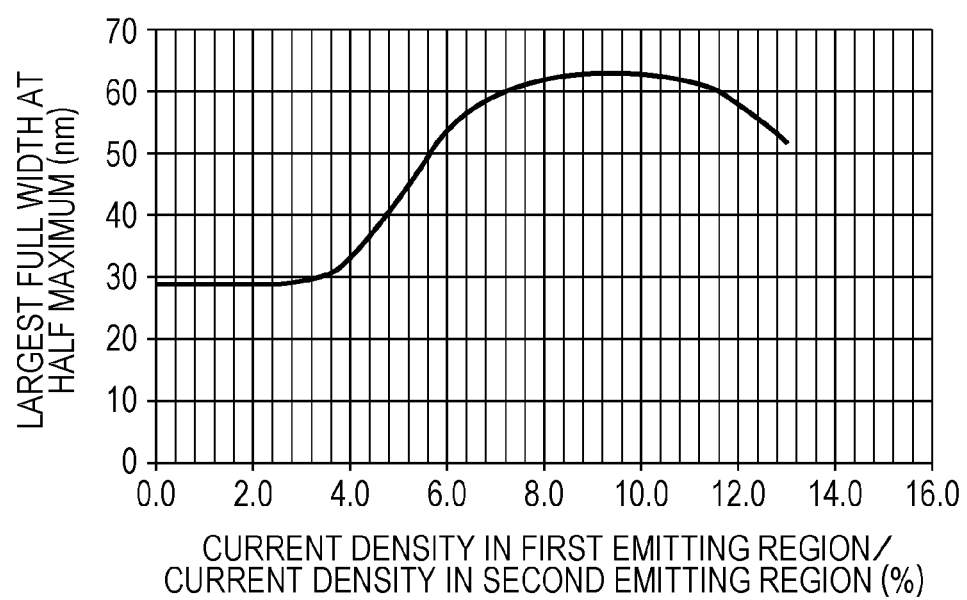
FIG. 10 is a graph showing a relationship between "current density in first emitting region/current density in second emitting region" and the largest full width at half maximum of an emission spectrum obtained in EXAMPLE 1.

FIG. 10 is a graph showing a full width at half maximum of an emission spectrum obtained when the amount of current injected into the second emitting region was fixed at 110 mA (18.3 kA/cm$^2$) and the ratio of the density of current injected into the first emitting region to the density of current injected into the second emitting region was varied. The graph shows that the full width at half maximum increases when the ratio of the density of current injected into the first emitting region ranges from 3% to about 10%, and decreases when the current injection exceeds this. The horizontal axis of the graph of FIG. 10 represents "current density in first emitting region/current density in second emitting region", which is a value obtained by dividing a current density in the first emitting region by a current density in the second emitting region. That is, the horizontal axis of FIG. 10 represents the current density ratio. The same applies to the horizontal axes of the graphs of FIGS. 12 and 15.

To achieve a maximum resolution, the OCT apparatus including the light source described above may drive the light source such that the condition that maximizes the full width at half maximum of the spectrum is satisfied. That is, the light source may be driven such that the ratio of the density of current injected into the first emitting region to the density of current injected into the second emitting region is 9.6%. To achieve high image contrast by increasing the light output even at the cost of resolution, it may be possible to further increase the amount of current injected into the first emitting region.

The graph of FIG. 10 shows that an emission spectrum with a large full width at half maximum can be obtained when "current density in first emitting region/current density in second emitting region" is less than about 10%.

Example 2

Single Quantum Well Structure: Example of Two-Electrode SLD

Figure 11A:
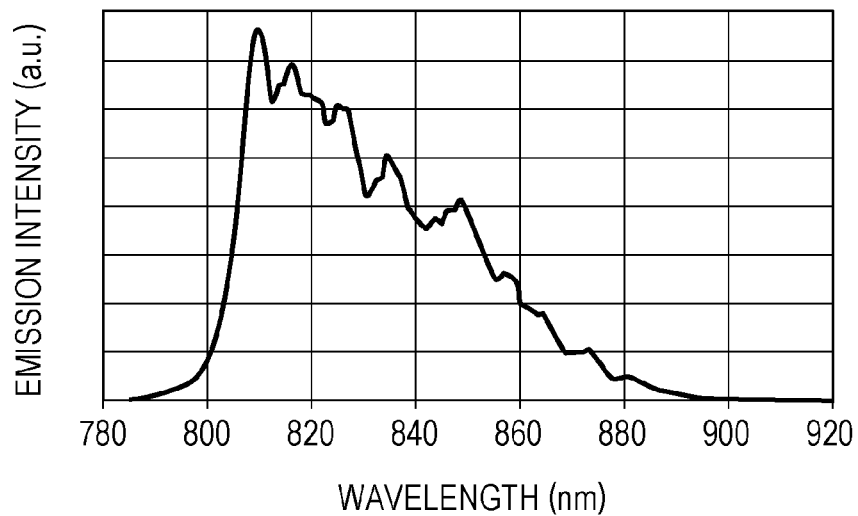
FIG. 11A is a graph of an emission spectrum obtained in EXAMPLE 2 of the present invention.
Figure 11B:
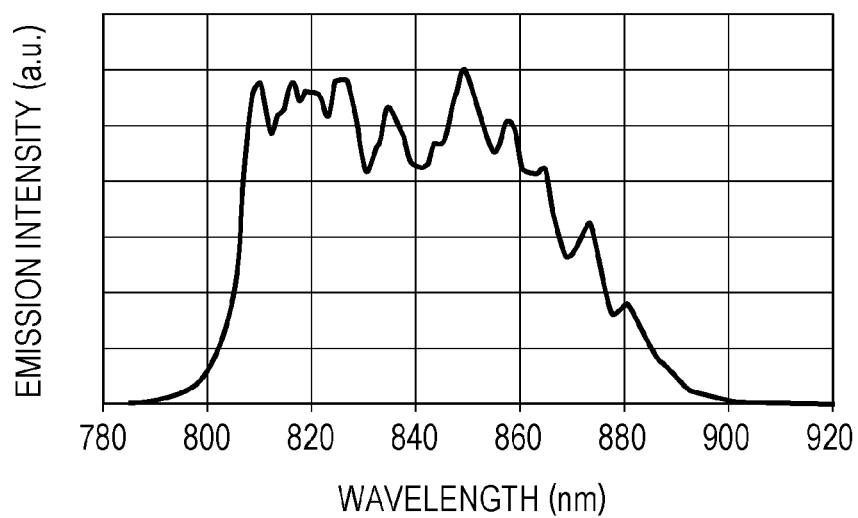
FIG. 11B is a graph of another emission spectrum obtained in EXAMPLE 2.
Figure 12:
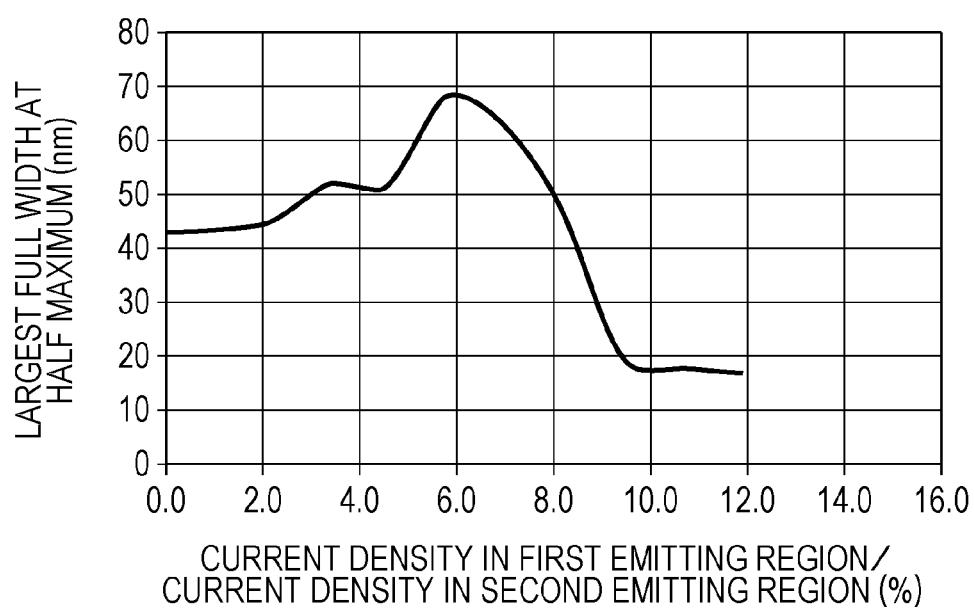
FIG. 12 is a graph showing a relationship between "current density in first emitting region/current density in second emitting region" and the largest full width at half maximum of an emission spectrum obtained in EXAMPLE 2.

With reference to FIGS. 11A and 11B and FIG. 12, an active layer having a quantum well structure different from that in EXAMPLE 1 will be described in EXAMPLE 2.

An active layer having a single quantum well structure was used in EXAMPLE 2. The active layer includes two $Al_{0.2}GaAs$ barrier layers and an 8-nm-thick $In_{0.07}GaAs$ well layer sandwiched therebetween. A 1-micrometer-thick $Al_{0.5}GaAs$ p-type cladding layer and a 1.2-micrometer-thick $Al_{0.5}GaAs$ n-type cladding layer were used.

A ridge portion was formed by a process similar to that of EXAMPLE 1. The ridge width was 3 micrometers, and the element lengths of a second electrode and a first electrode were 0.7 mm and 1.5 mm, respectively. The separation width between the first and second electrodes was 3 micrometers. The configuration of an insulating film and metal electrodes was similar to that of EXAMPLE 1.

Emission spectra of the light source formed by the process described above are shown in FIGS. 11A and 11B. FIG. 11A shows an emission spectrum obtained when a current of 400 mA (19.0 kA/cm$^2$) was injected into only a second emitting region. The full width at half maximum of this emission spectrum was 43 nm and the output was 8.9 mW. FIG. 11B shows an emission spectrum obtained when a current of 50 mA (1.11 kA/cm$^2$) was injected into a first emitting region in addition to the above-described injection of current into the second emitting region. The full width at half maximum of this emission spectrum was 68 nm and the light output was 13.2 mW, which are both greater than that in FIG. 11A. That is, by injecting a current into the first emitting region at a current density about 5.8% of that for the second emitting region, the full width at half maximum of the spectrum and the light output were increased by about 1.2 times and about 1.5 times, respectively, those in FIG. 11A.

FIG. 12 is a graph showing a full width at half maximum of an emission spectrum obtained when the amount of current injected into the second emitting region was fixed at 400 mA (19.0 kA/cm$^2$) and the ratio of the density of current injected into the first emitting region to the density of current injected into the second emitting region was varied. The graph shows that the full width at half maximum reaches its largest value when the ratio of the density of current injected into the first emitting region is around 6%.

The graph of FIG. 12 shows that the greater the "current density in first emitting region/current density in second emitting region" is than about 6%, the smaller the full width at half maximum. In other words, an emission spectrum with a large full width at half maximum can be obtained when "current density in first emitting region/current density in second emitting region" is less than about 6%.

EXAMPLES 1 and 2 have shown that the emission spectrum of the SLD with two electrodes increases in both the asymmetric multiple quantum well structure (two wells) and the single quantum well structure.

The table of FIG. 13 shows the conditions of current injection into the second emitting region and the first emitting region for achieving the largest full width at half maximum of the spectrum when the quantum well structure, the ridge width of the optical waveguide, and the element length are varied. The table shows that in any of the two-electrode SLDs, the full width at half maximum reaches its largest value when the ratio of the density of current injected into the first emitting region to the density of current injected into the second emitting region is less than 11%. Even in the case of giving priority to the light output as in FIG. 10 of EXAMPLE 1, the SLD light source is found to be effective as a light source that can improve image quality of the OCT apparatus when the ratio of current density described above is less than 44%.

Example 3

Asymmetric Multiple Quantum Well Structure: Example of Four-Electrode SLD

With reference to FIG. 7 and FIGS. 14A to 14C, an active layer having a quantum well structure different from that in EXAMPLE 1 will be described in EXAMPLE 3. Four electrodes were used in EXAMPLE 3.

In EXAMPLE 3, the quantum well structure of the active layer was an asymmetric structure that includes three 8-nm-thick quantum wells of $Al_{0.015}GaAs$, GaAs, and $In_{0.04}$ GaAs, each sandwiched between $Al_{0.2}GaAs$ layers. Both n-type and p-type cladding layers were 0.5-micrometer-thick $Al_{0.5}GaAs$ layers.

The ridge portion 106 was formed by a process similar to that of EXAMPLE 1. A ridge width 601 in the first electrode 110, the second electrode 120, the third electrode 630, and the fourth electrode 640 was 5 micrometers. An element length 621 of the second electrode 120 was 0.25 mm, and element lengths 611, 631, and 641 of the first, third, and fourth electrodes 110, 630, and 640, respectively, were all 0.5 mm, and a separation width between two adjacent electrodes was 10 micrometers. The configuration of an insulating film and metal electrodes was similar to that of EXAMPLE 1.

Figure 14A:
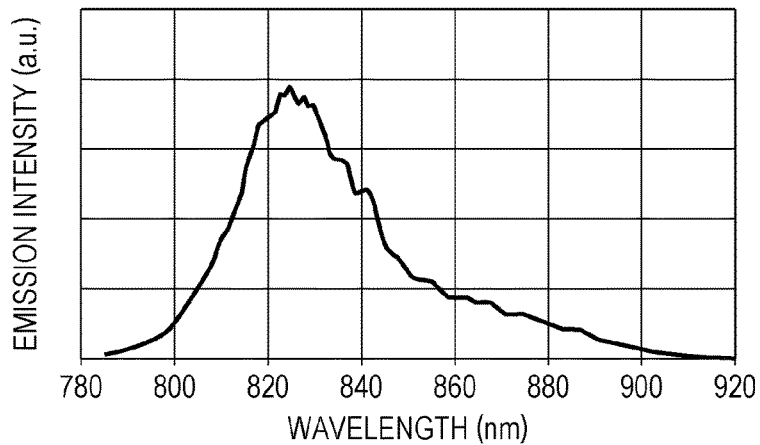
FIG. 14A is a graph of an emission spectrum obtained in EXAMPLE 3 of the present invention.
Figure 14B:
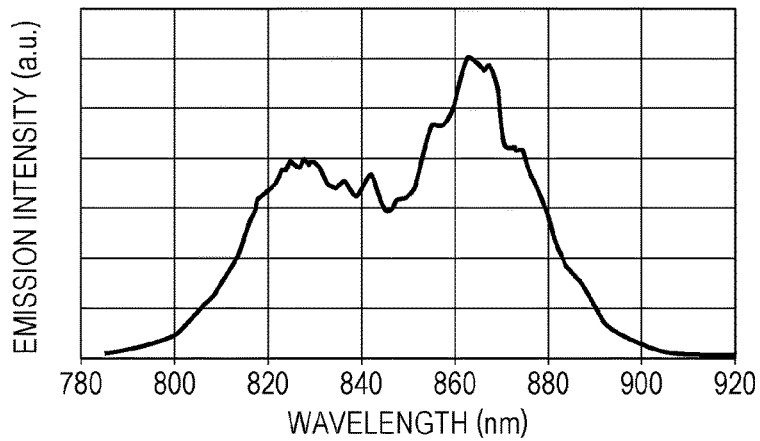
FIG. 14B is a graph of another emission spectrum obtained in EXAMPLE 3.
Figure 14C:
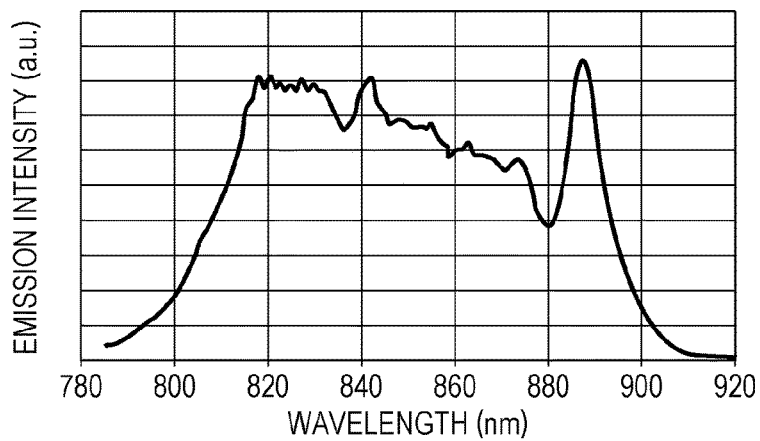
FIG. 14C is a graph of another emission spectrum obtained in EXAMPLE 3.

Emission spectra of the light source formed by the process described above are shown in FIGS. 14A to 14C. FIG. 14A shows an emission spectrum obtained when a current of 180 mA (14.4 kA/cm$^2$) was injected into only the second emitting region. The full width at half maximum of this emission spectrum was about 32 nm FIG. 14B shows an emission spectrum obtained when a current of 180 mA (14.4 kA/cm$^2$) was injected into the second emitting region and a current of 28 mA (1.12 kA/cm$^2$) was injected into the first emitting region. This emission spectrum has the largest full width at half maximum that can be obtained by two-electrode control. Here, the ratio of the density of current injected into the first emitting region to the density of current injected into the second emitting region was 7.8%. The full width at half maximum of the emission spectrum was doubled to 63 nm FIG. 14C shows an emission spectrum obtained when a current of 180 mA (14.4 kA/cm$^2$) was injected into the second emitting region again, a reduced current of 4.2 mA (0.17 kA/cm$^2$) was injected into the first emitting region, and a current of 0 mA and a current of 180 mA (14.4 kA/cm$^2$) were injected into the third emitting region and the fourth emitting region, respectively. The full width at half maximum of this emission spectrum was 85 nm. The ratio of the density of current injected into the first emitting region to the density of current injected into the second emitting region was 1.2%.

Example 4

Example 1 Performed with Wiring Resistance

EXAMPLE 4 uses an SLD that has the same active layer structure, the same waveguide structure, and the same electrode division ratio as those in EXAMPLE 1, but is different in the method of current injection. EXAMPLE 4 will be described with reference to FIG. 4.

To obtain an emission spectrum having a wide full width at half maximum in EXAMPLE 1, a current of 110 mA (18.3 kA/cm$^2$) and a current of 14 mA (1.75 kA/cm$^2$) were injected, from an independent power supply (not shown), into the second emitting region and the first emitting region, respectively. In EXAMPLE 4, as illustrated in FIG. 4, the metal wire 301 for current injection into the second emitting region was extended, and the wiring resistance of the metal wire 301 was used to inject a current of 14 mA (1.75 kA/cm$^2$) into the first emitting region.

When a current is injected from a power supply through a metal wire into a semiconductor, there are a contact resistance between the metal and the semiconductor, and an internal resistance of the diode. An estimation based on current-voltage characteristics found that the resistances were 10.9 ohms The resulting calculation showed that a current of 14 mA could be injected into the first emitting region by forming a wiring resistance of 74.7 ohms between the second emitting region and the first emitting region. This determined that the metal wire 301 formed to a thickness of Ti (50 nm)/Au (300 nm) was 5 micrometers in width and 350 nm x 5 micrometers in cross-sectional area. For simplicity, the calculation was made on the assumption that the metal wire 301 was entirely made of Au and the resistivity of Au was 2.4×10$^{-6}$ ohm cm. Thus, the length of the metal wire 301 was calculated as 0.545 cm. The metal wire 301 was formed into a pattern and connected to the first emitting region.

Thus, an emission spectrum substantially identical to that in EXAMPLE 1 was obtained. Generally, driving an SLD having a multi-electrode structure requires multiple power supply channels. However, the driving method of EXAMPLE 4 makes it possible to drive the SLD with a single power supply.

Example 5

Example 1 Performed with Diffusion Resistance (Semiconductor Layer)

EXAMPLE 4 has described a method in which a resistance of a metal wire from the second emitting region of the SLD is used to inject a predetermined current into the first emitting region. With reference to FIGS. 5A and 5B, EXAMPLE 5 will describe a method in which a resistance of a semiconductor contact layer is used to inject a current into the first emitting region.

To form a multi-electrode structure, as illustrated in FIGS. 2A and 2B, the upper electrode 108 on the ridge and the contact layer (heavily doped GaAs layer) 104 under the upper electrode 108 were partially removed to electrically separate the second electrode 120 and the first electrode 110.

In EXAMPLE 5, although the upper electrode 108 was partially removed as illustrated in FIGS. 5A and 5B, the contact layer 404 under the upper electrode 108 was left unchanged. Here, the resistance of the contact layer 404 serves as a resistance of the metal wire described above.

An SLD having the same structure as that of the SLD in EXAMPLE 1 was formed as illustrated in FIG. 5B. However, although Au and Ti of the upper electrode 108 were removed to divide the upper electrode 108, the heavily doped GaAs layer (contact layer 404) was not etched and was left unchanged. The heavily doped GaAs layer is a GaAs layer doped with carbon (C) impurities at a concentration of 5×10$^{19}$ cm$^{-3}$, which is equivalent to a resistivity of 2×10$^{-3}$ ohm cm. Resistance R can be expressed as R=rho x L/A, where rho is resistivity, L is resistor length, and A is resistor cross-sectional area. To provide a resistance equivalent to that of the wiring resistance (74.7 ohms) in EXAMPLE 4 by using the contact layer 404, a heavily doped GaAs layer 5 micrometers wide and 0.2 micrometers thick needs to be 3.74 micrometers long. Therefore, the separation width between the first electrode 110 and the second electrode 120 (i.e., the width of the dividing portion 109) was 3.74 micrometers.

Injecting a current of 110 mA (18.3 kA/cm$^2$) into only the second emitting region of the light source produced a spectrum substantially identical to that in EXAMPLE 1.

Example 6

Example 1 with First and Second Electrodes Having Different Ridge Widths

EXAMPLE 6 deals with an SLD having the same active layer structure as that in EXAMPLE 1, but having the first and second electrodes 110 and 112 with different ridge widths. EXAMPLE 6 will be described with reference to FIG. 6.

A light source having a ridge waveguide was formed by a process similar to that of EXAMPLE 1. Differences from the light source of EXAMPLE 1 are that the ridge width 501 of the first electrode 110 was 8 micrometers, which is double the ridge width 502 of the second electrode 120, and that the ridge width was changed at the dividing portion between the second electrode 120 and the first electrode 110. The ridge width and the element length of the second electrode 120 and the element length of the first electrode 110 were the same as those of the light source of EXAMPLE 1.

With the amount of current injected into the second emitting region fixed at 110 mA (18.3 kA/cm$^2$), changes in full width at half maximum of the emission spectrum were observed while the amount of current injected into the first emitting region was gradually changed from 0. The full width at half maximum reached its largest value of 64 nm when the amount of current injected into the first emitting region was 20 mA (1.25 kA/cm$^2$). The ratio of the density of current injected into the first emitting region to the density of current injected into the second emitting region was 6.8%. The light output was 2.3 mW, which is slightly higher than that in EXAMPLE 1.

Example 7

Figure 15:
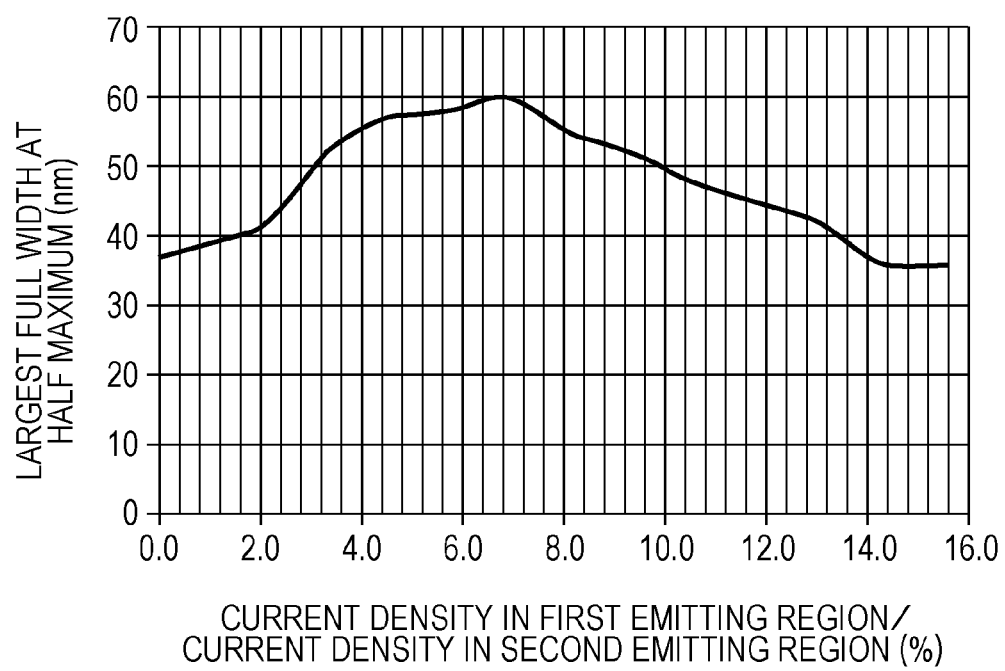
FIG. 15 is a graph showing a relationship between "current density in first emitting region/current density in second emitting region" and the largest full width at half maximum of an emission spectrum obtained in EXAMPLE 7 of the present invention.

In EXAMPLE 7, an emission spectrum of a light source was measured, which is the same as that in EXAMPLE 1 except that the element length of the first and second electrodes was 0.2 mm, the ridge width was 4 micrometers, and the density of current injected into the second emitting region was 20013 A/cm$^2$. FIG. 15 is a graph showing a relationship between "current density in first emitting region/current density in second emitting region" and the largest full width at half maximum of the emission spectrum obtained in EXAMPLE 7.

The graph of FIG. 15 shows that the greater the "current density in first emitting region/current density in second emitting region" is than about 7%, the smaller the full width at half maximum. In other words, an emission spectrum with a large full width at half maximum can be obtained when "current density in first emitting region/current density in second emitting region" is less than about 7%.

On the other hand, the light output increases as "current density in first emitting region/current density in second emitting region" increases. Therefore, for example, when "current density in first emitting region/current density in second emitting region" is less than 44%, a light source suitable for use in the OCT apparatus can be realized.

Example 8

Figure 16A:
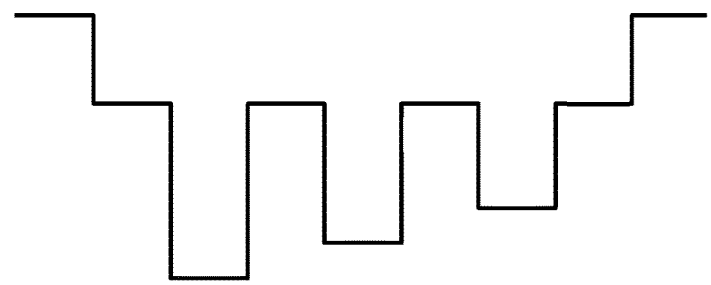
FIG. 16A is a diagram for explaining EXAMPLE 8 of the present invention.

A light source of EXAMPLE 8 will be described with reference to FIG. 1, etc. In EXAMPLE 8, in the first embodiment (FIG. 1 and FIGS. 2A and 2B), an n-type GaAs substrate was used as the substrate 100, an n-type cladding layer (n-$Al_{0.5}$GaAs, 1.2 micrometers thick) was used as the lower cladding layer 101, a p-type cladding layer (n-$Al_{0.5}$GaAs, 1 micrometer thick) was used as the upper cladding layer 103, and a p-type contact layer (p-GaAs doped with carbon (C) impurities at a concentration of $5 \times 10^{19}$ $cm^{-3}$, 0.2 micrometers thick) was used as the contact layer 104. As illustrated in FIG. 16A, the active layer 102 having an asymmetric multiple quantum well structure (asymmetric triple quantum well structure or asymmetric multiple quantum well structure 1 illustrated in FIG. 19) composed of three depth-modulated quantum wells was used. Specifically, the active layer 102 includes three 8-nm-thick $In_{0.04}$GaAs, GaAs, and $Al_{0.015}$GaAs well layers and two barrier layers ($Al_{0.02}$GaAs, 8 nm thick) alternately disposed.

The ridge portion 106 was formed into a structure having a ridge width of 3 micrometers and a height of 0.75 micrometers, by forming a striped resist pattern using a photolithographic technique and then partially etching the contact layer 104 and the upper cladding layer 103.

After a 0.4-micrometer-thick $SiO_2$ film 105, which is an insulating film, was formed by sputtering over the entire surface of the upper cladding layer 103, only a portion of the contact layer 104 in the upper part of the ridge was exposed, and the upper electrode 108 was formed by a liftoff process. Next, the lower electrode 107 was formed on the entire lower surface of the substrate 100. The upper electrode 108 and the lower electrode 107, which are a Ti (50 nm)/Au (300 nm) stacked film and an AuGe (150 nm)/Ni (30 nm)/Au (200 nm) stacked film, respectively, were formed by a vacuum evaporation method.

Last, to allow the first electrode 110 and the second electrode 120 to be independently driven, the upper electrode 108 and the contact layer 104 were partially removed by etching at the dividing portion 109 in the photolithography and etching process. Thus, the upper electrode 108 was divided into the first electrode 110 and the second electrode 120.

The element lengths of the first electrode 110 and the second electrode 120 electrically separated from each other were both 0.4 mm. The separation width between the electrodes was 10 micrometers.

To prevent reflection of emitted light, the ridge portion 106 was structured such that the longitudinal direction thereof was inclined 7 degrees from the normal to an end face (cleavage plane) thereof.

Figure 16B:
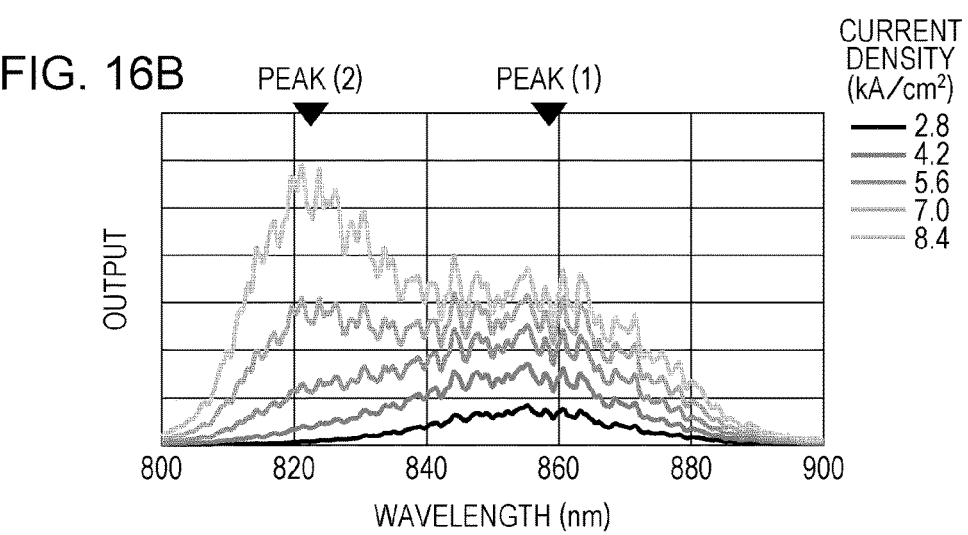
FIG. 16B is another diagram for explaining EXAMPLE 8.

For the light source formed by the process described above, first, a current was injected into only the second emitting region. Then, the characteristics of the SLD with a single-electrode configuration were evaluated. The result is shown in FIG. 16B. In the active layer, a peak of higher energy level emission (1) appears at 858 nm, and a peak of lower energy level emission (2) appears at 824 nm. The current density at which light of higher energy level begins to emit is 5.6 $kA/cm^2$.

Figure 17:
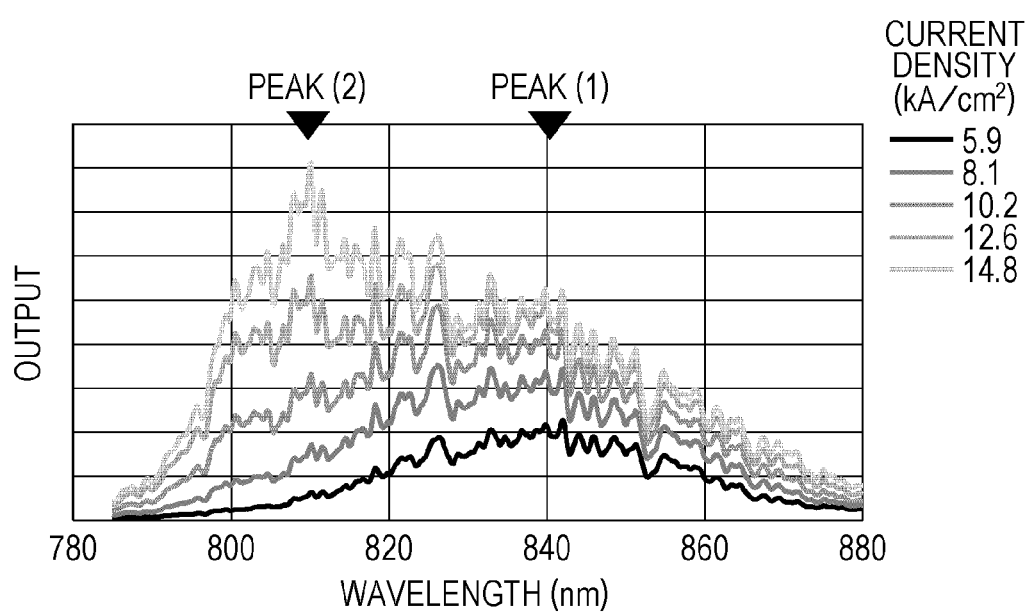
FIG. 17 is another diagram for explaining EXAMPLE 8.

For comparison, FIG. 17 shows characteristics of a similarly prepared SLD in which the active layer has a single quantum well structure. The second electrode 120 is 0.4 mm long, and conditions other than the structure of the active layer are the same as those of the SLD in EXAMPLE 1. In this active layer, a peak of lower energy level emission (1) appears at 840 nm, and a peak of higher energy level emission (2) appears at 810 nm. The current density at which light of higher energy level begins to emit is 10.2 $kA/cm^2$.

The current density at which light of higher energy level begins to emit when the active layer having the asymmetric multiple quantum well structure 1 (see FIG. 19) is used is about 0.55 times that in the case of the single quantum well structure. That is, the current density necessary to emit light of higher energy level is smaller than that in the case of using the single quantum well structure.

Figure 16C:
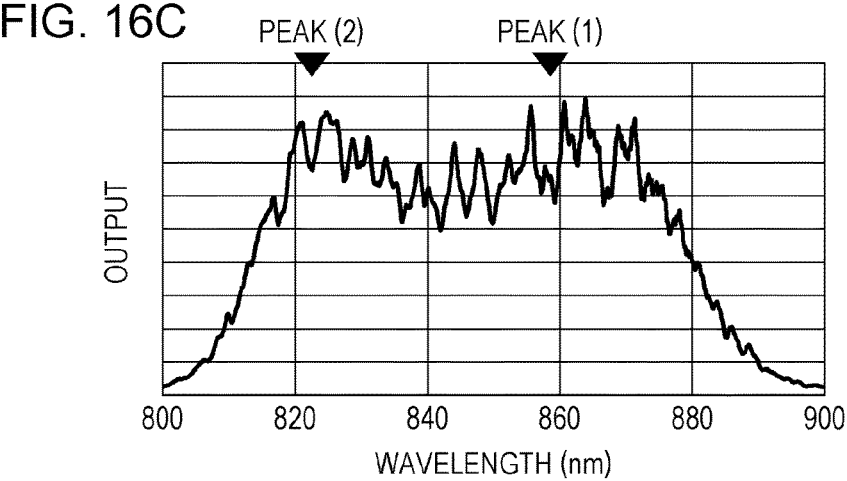
FIG. 16C is another diagram for explaining EXAMPLE 8.

FIG. 16C shows how the spectrum changes when the second emitting region is SLD-operated and current is gradually injected into the first emitting region. The widest wavelength range was obtained when the current density in the first emitting region was 0.6 $kA/cm^2$ and the current density in the second emitting region was 15.3 $kA/cm^2$. The full width at half maximum of the spectrum was 64 nm. Thus, a higher output and a wider emission wavelength range were achieved, as compared to the SLD having a single-electrode configuration.

Here, being SLD-operated refers to a state where stimulated amplification occurs. This occurs when the carrier density becomes greater than or equal to the transparent carrier density. The reason for SLD-operating the second emitting region is to emit light of higher energy level from the second emitting region. In FIG. 16C, the current density in the second emitting region is about 96% of the saturated current density in a single electrode. This ratio may need to be 80% or more to facilitate amplification of light from the first emitting region. Note that the saturated current density is a current density for the amount of current injection reached when the light output no longer increases even if current continues to be injected in the SLD with a single electrode configuration.

In the SLD having a multi-electrode configuration, a basic driving condition for realizing a high output and a wide wavelength range is to emit light of higher energy level from the second emitting region and to emit light of lower energy level from the first emitting region. This is because since the intensity of lower energy level emission is lower than that of higher energy level emission, the light of lower energy level is amplified by passing through the second emitting region to the same level as that of the light of higher energy level. Therefore, in the SLD with a multi-electrode configuration, it is necessary to increase the density of current injected into the second emitting region. The widest spectrum is achieved when the intensity of higher energy level emission and that of lower energy level emission are substantially the same.

As described above, an adjustment may be made such that light of higher energy level is emitted from the second emitting region and light of lower energy level is emitted from the first emitting region.

Example 9

Figure 18A:
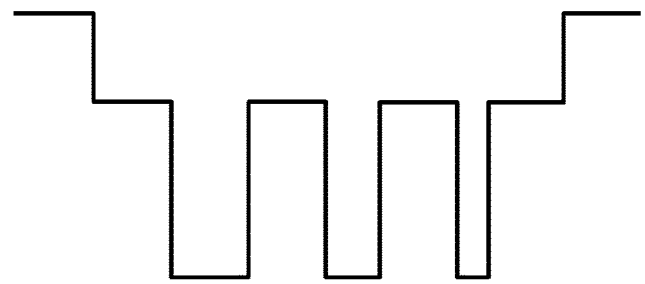
FIG. 18A is a diagram for explaining EXAMPLE 9 of the present invention.

EXAMPLE 9 uses an active layer having an asymmetric multiple quantum well structure illustrated in FIG. 18A. As illustrated, the active layer having an asymmetric multiple quantum well structure (asymmetric triple quantum well structure) composed of three depth-modulated quantum wells was used. Specifically, the active layer includes three $In_{0.04}GaAs$ well layers (8 nm, 6 nm, and 4 nm thick) and two barrier layers ($Al_{0.02}GaAs$, 8 nm thick) alternately disposed. The first electrode and the second electrode were both 0.4 mm long, and the other conditions were also the same as those of the SLD of EXAMPLE 1.

Figure 18B:
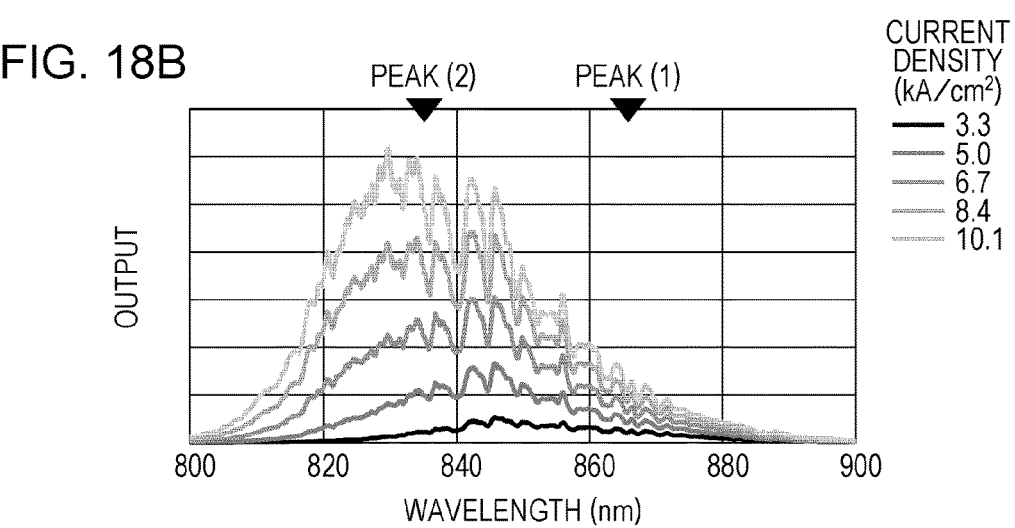
FIG. 18B is another diagram for explaining EXAMPLE 9.

For the light source formed by the process described above, first, a current was injected into only the second emitting region. Then, the characteristics of the SLD with a single-electrode configuration were evaluated. The result is shown in FIG. 18B. In the active layer, a peak of lower energy level emission (1) appears at 866 nm, and a peak of higher energy level emission (2) appears at 836 nm. The current density at which light of higher energy level begins to emit is 6.7 $kA/cm^2$.

The current density at which light of higher energy level begins to emit when the active layer having the asymmetric multiple quantum well structure 2 (see FIG. 19) is used is about 0.66 times that in the case of the single quantum well structure. That is, the current density necessary to emit light of higher energy level is smaller than that in the case of using the single quantum well structure.

Figure 18C:
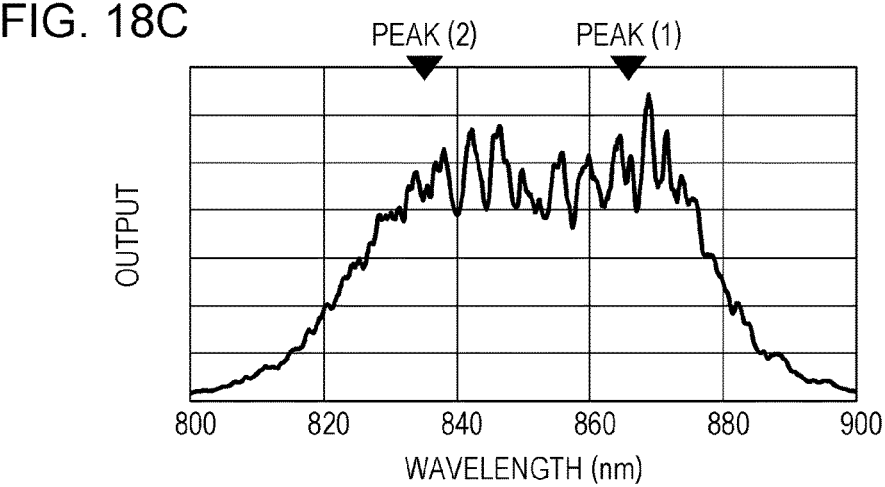
FIG. 18C is another diagram for explaining EXAMPLE 9.

FIG. 18C shows how the spectrum changes when the second emitting region is SLD-operated and current is gradually injected into the first emitting region. The widest wavelength range was obtained when the current density in the first emitting region was 3.9 $kA/cm^2$ and the current density in the second emitting region was 17.0 $kA/cm^2$. The full width at half maximum of the spectrum was 58 nm. Thus, a higher output and a wider emission wavelength range were achieved, as compared to the SLD having a single-electrode configuration.

FIG. 19 is a table showing minimum current densities necessary to emit light of higher energy level in the asymmetric multiple quantum well structures of EXAMPLES 8 and 9 and a single quantum well structure. The table shows that by using an asymmetric multiple quantum well structure, instead of a single quantum well structure, as an active layer structure, the minimum current density necessary to emit light of first-order (higher energy) level can be reduced.

Example 10

EXAMPLE 10 describes an SLD that includes four electrodes, as in EXAMPLE 3. Differences from EXAMPLE 3 are that the element lengths of the second electrode, the first electrode, the third electrode, and the fourth electrode are 0.33 mm, 0.3 mm, 1.5 mm, and 0.25 mm, respectively. The ridge width is 5 micrometers.

In EXAMPLE 10, the minimum current density necessary to emit light of first-order (higher energy) level was 7.5 $kA/cm^2$. Thus, in the SLD of EXAMPLE 10, the minimum current density necessary to emit light of first-order (higher energy) level is low.

Figure 20A:
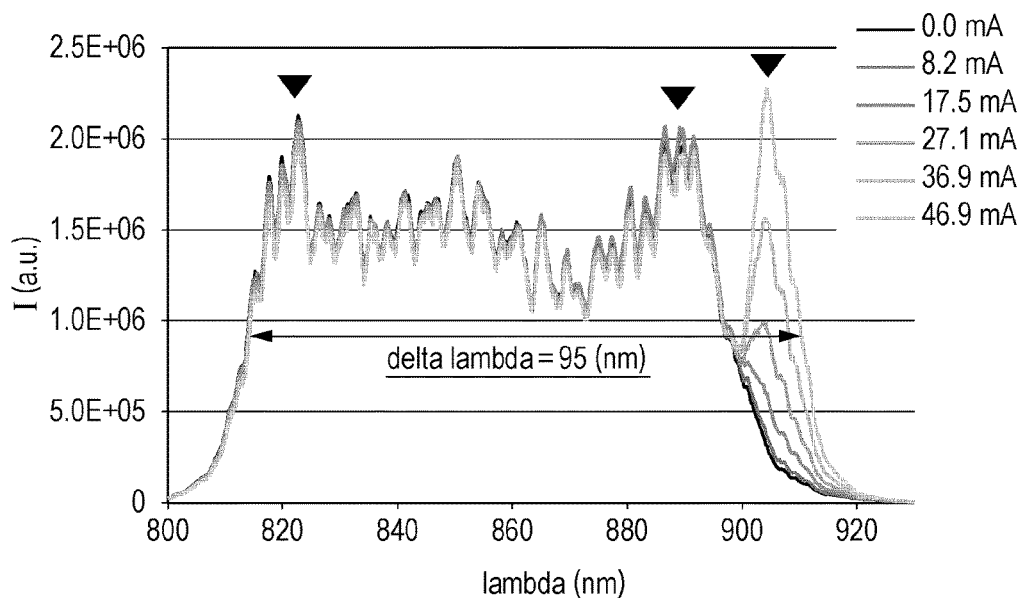
FIG. 20A is a diagram for explaining EXAMPLE 10 of the present invention.
Figure 20B:
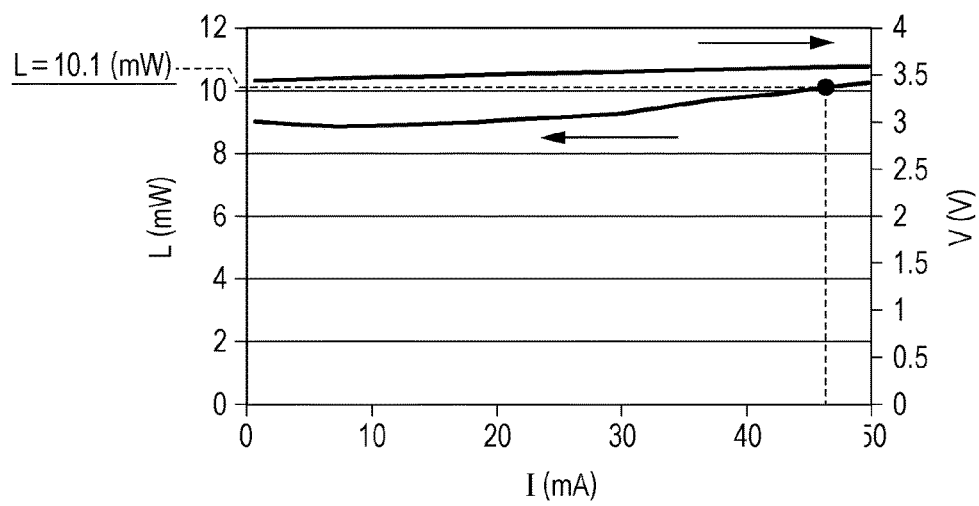
FIG. 20B is another diagram for explaining EXAMPLE 10.

FIG. 20A is a graph showing how the intensity of the emission spectrum of the SLD according to EXAMPLE 10 changes when the current injected into the fourth emitting region is varied. FIG. 20B is a graph showing the measured intensity of the output light of the SLD according to EXAMPLE 10. These graphs show that the SLD of EXAMPLE 10 has a wide emission wavelength range and can output light of high intensity.

The present invention can provide a light source in which the minimum current density necessary to emit light of first-order (higher energy) level is small.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application is a national phase application of international application PCT/JP2013/005693, filed on Sep. 26, 2013, which is hereby incorporated by reference herein in its entirety, and this application claims the benefit of Japanese Patent Application No. 2012-217190, filed Sep. 28, 2012, which is hereby incorporated by reference herein in its entirety.

The invention claimed is:

1. A super luminescent diode comprising:
   a first electrode layer which includes a first electrode and a second electrode;
   a second electrode layer;
   an active layer interposed between the first electrode layer and the second electrode layer; and
   a control unit configured to control current injected into the first electrode and the second electrode,
   wherein the first electrode and the second electrode is disposed in an in-plane direction of the active layer;
   wherein the first electrode and the second electrode are configured to independently inject current into a plurality of different regions in the active layer;
   wherein the plurality of different regions in the active layer include a first region not including a light exit end of the super luminescent diode and a second region including the light exit end of the super luminescent diode;
   wherein the active layer has an asymmetric multiple quantum well structure;
   wherein light emitted from the first region and passed through the second region is output from the super luminescent diode; and
   wherein the control unit is configured to perform the control such that a density of current injected into the first electrode is less than 14% of a density of current injected into the second electrode.

2. The super luminescent diode according to claim 1, wherein a carrier density in the second region is greater than a transparent carrier density.

3. The super luminescent diode according to claim 1, wherein the second region has a dominant peak at an energy level higher than that of a dominant peak of light incident on the second region.

4. The super luminescent diode according to claim 1, wherein a current density in the second region is greater than or equal to 80% of a saturated current density.

5. The super luminescent diode according to claim 1, wherein the control unit is configured to control a density of current injected into the first electrode so that the density of current injected into the first electrode is less than 11% of a density of current injected into the second electrode.

6. The super luminescent diode according to claim 1, wherein the control unit is configured to control a density of current injected into the first electrode so that the density of current injected into the first electrode is more than 0% of a density of current injected into the second electrode.

7. The super luminescent diode according to claim 1, wherein the control unit is configured to control a density of current injected into the first electrode so that the density of current injected into the first electrode is more than or equal to 3% of a density of current injected into the second electrode.

8. The super luminescent diode according to claim 1, wherein the first region and the second region each independently have an asymmetric multiple quantum well structure, and include a quantum well capable of emitting light at two or more different quantum levels.

9. The super luminescent diode according to claim 1, wherein the first region and the second region have the same active layer.

10. The super luminescent diode according to claim 1, wherein the first electrode and the second electrode are electrically connected to each other by a resistance element; and
current is injected into the second region and the first region by applying a voltage to the second electrode.

11. The super luminescent diode according to claim 1, wherein the first electrode and the second electrode are electrically connected to each other by a semiconductor layer; and
current is injected into the second region and the first region by applying a voltage to the second electrode.

12. The super luminescent diode according to claim 1, wherein the control unit performs control such that the second largest peak value of a point spread function of an emission spectrum of light emitted from the first region and passed through the second region is less than or equal to 30% of the largest peak value.

13. An optical coherence tomography apparatus comprising:
the super luminescent diode according to claim 1;
an interference optical system configured to divide light from the super luminescent diode into reference light and irradiation light operable to irradiate and be reflected from an object, and generate interference light based on the reference light and the reflected irradiation light;
a wavelength dispersing unit configured to disperse a wavelength of the interference light;
a light detecting unit configured to receive the interference light whose wavelength has been dispersed; and
an information obtaining unit operable to obtain information about the object on the basis of an intensity of the interference light.

14. The super luminescent diode according to claim 1, wherein an emission spectrum of light which is output from the super luminescent diode, has a substantially Gaussian shape.

15. The super luminescent diode according to claim 1, further comprising
a first contact layer which is disposed between the first electrode and the active layer;
a second contact layer which is disposed between the second electrode and the active layer;
wherein the first contact layer contacts the first electrode, the second contact layer contacts the second electrode, and the first contact layer and the second contact layer are spaced apart.

16. The super luminescent diode according to claim 1, wherein the first region emits light of at least ground level and the second region emits light of at least first-order level.

\* \* \* \* \*